(12) United States Patent
Nonoguchi et al.

(10) Patent No.: US 8,039,651 B2
(45) Date of Patent: Oct. 18, 2011

(54) METHOD FOR PRODUCING FATTY ACID ALKYL ESTER AND/OR GLYCERIN

(75) Inventors: Masanori Nonoguchi, Ibaraki (JP); Hiroko Izumi, Ibaraki (JP); Atsushi Tachibana, Osaka (JP); Tomoharu Oku, Osaka (JP); Toshimitsu Moriguchi, Osaka (JP); Takeo Akatsuka, Osaka (JP); Izuho Okada, Osaka (JP); Hideaki Tsuneki, Osaka (JP); Hironori Horie, Hyogo (JP)

(73) Assignee: Nippon Shokubai Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 12/739,332

(22) PCT Filed: Oct. 31, 2007

(86) PCT No.: PCT/JP2008/070151
§ 371 (c)(1),
(2), (4) Date: Apr. 22, 2010

(87) PCT Pub. No.: WO2009/057810
PCT Pub. Date: May 7, 2009

(65) Prior Publication Data
US 2010/0249441 A1    Sep. 30, 2010

(30) Foreign Application Priority Data

Oct. 31, 2007  (JP) ................ 2007-284402
Oct. 31, 2007  (JP) ................ 2007-284403
Dec. 26, 2007  (JP) ................ 2007-335303

(51) Int. Cl.
*C07C 67/00* (2006.01)
(52) U.S. Cl. ......... 554/124; 422/187; 422/211; 568/858
(58) Field of Classification Search ............... 554/124; 422/187, 211; 568/858
See application file for complete search history.

(56) References Cited

U.S. PATENT DOCUMENTS

| 5,508,457 | A | 4/1996 | Bayense et al. |
| 5,908,946 | A | 6/1999 | Stern et al. |
| 5,972,057 | A | 10/1999 | Hayafuji et al. |
| 7,605,281 | B2 | 10/2009 | Oku et al. |
| 2004/0034244 | A1 | 2/2004 | Bournay et al. |
| 2005/0113588 | A1 | 5/2005 | Hillion et al. |
| 2007/0167642 | A1* | 7/2007 | Oku et al. ............ 554/174 |
| 2009/0069586 | A1 | 3/2009 | Oku et al. |

FOREIGN PATENT DOCUMENTS

JP    2005-177722 A    7/2005

* cited by examiner

*Primary Examiner* — Deborah D Carr
(74) *Attorney, Agent, or Firm* — Connolly Bove Lodge & Hutz LLP

(57) ABSTRACT

In the method of the present invention for producing fatty acid alkyl ester and/or glycerin, as a heat source for an alcohol refining step of refining alcohol from unreacted alcohol that remains without reacting in a first reaction step, at least a part of heat of the unreacted alcohol is used. This allows reducing costs in production of fatty acid alkyl ester and/or glycerin over a solid catalyst.

20 Claims, 3 Drawing Sheets

METHOD FOR PRODUCING FATTY ACID ALKYL ESTER AND/OR GLYCERIN

CROSS REFERENCE TO RELATED APPLICATIONS

This application is a National Phase filing under 35 U.S.C. §371 of PCT/JP2008/070151 filed Oct. 29, 2008, which claims priority to JP 2007-284402 filed Oct. 31, 2007, JP 2007-284403 filed Oct. 31, 2007 and JP 2007-335303 filed Dec. 26, 2007, the entire contents of all are hereby incorporated by reference.

TECHNICAL FIELD

The present invention relates to a method for producing fatty acid alkyl ester and/or glycerin. Specifically, the present invention relates to recycling of alcohol that is one of raw materials used in producing fatty acid alkyl ester and/or glycerin.

BACKGROUND ART

Fatty acid alkyl ester is widely used in the fields of cosmetics and medicines, as well as fatty acid alkyl ester derived from animal fats and vegetable oils is used in foods. Further, attention is paid to fatty acid alkyl ester serving as a fuel to be added to gas oil. In other words, this is a biodiesel fuel derived from animal fats and vegetable oils, which has been developed in order to reduce the amount of carbon dioxide to be exhausted. Fatty acid alkyl ester is directly used as a substitute for gas oil etc., or used as a fuel to be added to gas oil etc. with a certain ratio. The biodiesel fuel has various advantages such that it gives less damage to environment compared with a conventional diesel fuel derived from petroleum.

Further, glycerin is used mainly as a raw material for nitroglycerin, and also used in various fields such as a raw material for alkyd resin, medicines, foods, printing ink, cosmetics etc.

An example of a method for producing such fatty acid alkyl ester and glycerin is a method in which triglyceride that is a main component of fat and oil is subjected to ester exchange with alcohol.

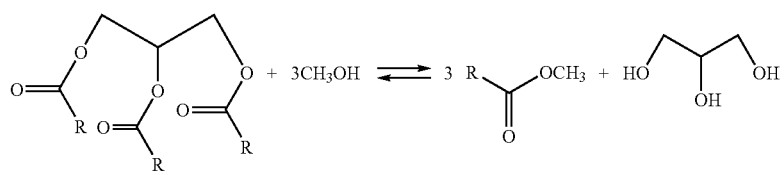

[Chemical Formula 1]

where R represents an alkyl group having 6-22 carbon atoms or an alkenyl group having 6-22 carbon atoms with one or more unsaturated bonding.

In general, as the method with use of a transesterification between fats and oils and alcohols, a method using a homogeneous alkaline catalyst is industrially used.

However, usage of a homogeneous alkaline catalyst makes a step of separating and removing a catalyst complicated. Further, free fatty acid included in fat and oil is saponified by the alkaline catalyst and consequently a soap is produced as a by-product. This requires a step of cleaning the soap with a large amount of water and decreases the yield of fatty acid alkyl ester due to emulsification of the soap. Further, a step of refining glycerin is complicated.

In order to solve the problem, there have been developed methods for producing fatty acid alkyl ester and/or glycerin over a solid catalyst instead of a homogeneous alkaline catalyst (see Patent Documents 1-5 for example). The method using the solid catalyst has a less complicated process, and has a less amount of wastes such as waste water and waste salts produced in the reaction, compared with the method using the homogeneous alkaline catalyst. Further, Patent Document 6 discloses a method for producing fatty acid alkyl ester and/or glycerin over a solid catalyst.

Production of fatty acid alkyl ester and glycerin over the solid catalyst does not require a complicated operation in its production process, and has a less amount of wastes such as waste water and waste salts produced in the reaction, compared with the method using the homogeneous alkaline catalyst.

However, in general, a transesterification is an equilibrium reaction. Therefore, both in a case of the homogeneous alkaline catalyst and a case of the solid catalyst, it is necessary to use an excessive amount of a raw material (alcohol in general) in order to obtain a high yield of a product.

Recently, in view of consideration on environment and reduction of costs for production, it is requested that a material that can be reused by reproduction is reused as far as possible. Therefore, in producing fatty acid alkyl ester and glycerin, it is requested that out of an excessive amount of alcohol used in the transesterification, unreacted alcohol that remains without being used in the reaction is separated and refined from a reaction liquid so as to be reused as a raw material. For example, Patent Document 7 discloses a method in which unreacted alcohol that remains without being used in a reaction is evaporated from a reaction liquid by a pressure flash and then refined as alcohol through evaporation and reused as a raw material for a transesterification.

Patent Document 1: Japanese Unexamined Patent Publication No. Tokukai 2005-200398 (published on Jul. 28, 2005)

Patent Document 2: Japanese Unexamined Patent Publication No. Tokukai 2006-225352 (published on Aug. 31, 2006)

Patent Document 3: Japanese Unexamined Patent Publication No. Tokukai 2005-177722 (published on Jul. 7, 2005)

Patent Document 4: Japanese Unexamined Patent Publication No. Tokukaihei 7-173103 (published on Jul. 11, 1995)

Patent Document 5: French Patent Publication No. 2752242, specification

Patent Document 6: Japanese Unexamined Patent Publication No. Tokukai 2005-206575 (published on Aug. 4, 2005)

Patent Document 7: U.S. Unexamined Patent Publication No. 2004/0034244, specification Patent Document 8: U.S. Unexamined Patent Publication No. 2005/0113588, specification

DISCLOSURE OF INVENTION

However, in producing fatty acid alkyl ester and glycerin, a process for reusing, as a raw material, unreacted alcohol that remains without being used in a reaction (the alcohol may be hereinafter referred to as "unreacted alcohol") requires a very large amount of energy. That is, the process separately requires a cost for producing the very large amount of energy and a cost for a device for producing the very large amount of energy. Consequently, in producing fatty acid alkyl ester and glycerin, it is difficult to sufficiently obtain the effect of reducing costs by reproducing and reusing alcohol.

The present invention was made in view of the foregoing problem. A main object of the present invention is to reduce production costs in producing fatty acid alkyl ester and glycerin over a solid catalyst. To be more specific, an object of the present invention is to reduce energy costs for reusing unreacted alcohol in producing fatty acid alkyl ester and glycerin.

In a conventional method for producing fatty acid alkyl ester and/or glycerin over a solid catalyst, unreacted alcohol in a reaction liquid is evaporated as needed through a general method including evaporation etc. This is because the method with use of the solid catalyst uses an excessive amount of alcohol compared with the method with use of the homogeneous alkaline catalyst, and does not have a step of removing alcohol through water washing.

In general, fatty acid alkyl ester and/or glycerin derived from animal fats and plant oils have a high boiling point. Consequently, when evaporating a small amount of alcohol remaining in the reaction liquid through evaporation etc., it is necessary to heat the reaction liquid at a high temperature. In this process, fatty acid alkyl ester and glyceride included in the reaction liquid are subjected to a transesterification, or fatty acid alkyl ester and glycerin are subjected to the transesterification and as a result a reverse reaction occurs in which fats and oils and alcohols are generated. The reverse reaction not only decreases the yield of fatty acid alkyl ester and/or glycerin but also generates glyceride that is a reaction intermediate, so that the purity of fatty acid alkyl ester that is an end product drops. In order to avoid a high temperature, evaporation in a high vacuum etc. is possible. However, since alcohol to be evaporated has a low boiling point in a high vacuum, it is necessary to increase the ability of cooling instrument for condensing the alcohol.

As described above, in the conventional method for producing fatty acid alkyl ester and/or glycerin, it is impossible to produce high-quality fatty acid alkyl ester and/or glycerin with a high yield and easiness. As such, a method for producing fatty acid alkyl ester and/or glycerin with a high yield and easiness is requested.

The present invention was made in view of the foregoing problems. An object of the present invention is to produce high-quality fatty acid alkyl ester and/or glycerin with a high yield and easiness.

In order to achieve the foregoing object, the inventors of the present invention paid attention to the fact that a transesterification using a solid catalyst is performed at a high temperature and under a high pressure. The inventors of the present invention have diligently studied and found that heat of unreacted alcohol evaporated from a reaction liquid obtained through the transesterification can be used as energy necessary for purifying alcohol from the unreacted alcohol, and completed the present invention.

The inventors further diligently studied and found that, when evaporating unreacted alcohol from a reaction liquid obtained by reacting fats and oils with alcohols, use of an evaporator including a heat exchanger with a short residence time increases the yield and purity of fatty acid alkyl ester that is an end product. Further, the inventors found that, when evaporating of alcohol in a glycerin phase that is obtained in the first phase-separation step is performed simultaneously with the evaporating of the unreacted alcohol, it is possible to increase purity of glycerin that is another end product. Further, the inventors have found that sufficiently evaporating alcohol before the second phase-separation step reduces distribution of fatty acid alkyl ester to the glycerin phase, and increases the yield of the fatty acid alkyl ester.

Further, in a case where a solid catalyst is used as a catalyst in producing fatty acid alkyl ester and/or glycerin as described above, there is a possibility that activity of the catalyst drops in a short time, which frequently requires troublesome exchanging of catalysts.

As an example for suppressing drop of activity of a solid catalyst, Patent Document 7 discloses a method for suppressing generation of free fatty acid in a transesterification system by restricting moisture concentration in fat and oil and alcohol. However, the method disclosed in Patent Document 7 cannot sufficiently suppress deterioration of a solid catalyst, and therefore cannot provide a sufficient period for the solid catalyst to perform well.

As described above, deterioration of a solid catalyst leads to preventing the increase in productivity of fatty acid alkyl ester and/or glycerin and preventing the cost reduction in producing fatty acid alkyl ester and/or glycerin. Therefore, there is a request for a method for producing fatty acid alkyl ester and/or glycerin while preventing deterioration in a solid catalyst.

The present invention was made in view of the foregoing problems. An object of the present invention is to provide a method for producing fatty acid alkyl ester and/or glycerin while sufficiently suppressing drop in activity of a solid catalyst, i.e., lengthening the life of the solid catalyst.

The inventors of the present invention have diligently studied what substance deteriorates a solid catalyst, and found that one of the causes for deterioration of a solid catalyst is covering of the surface of the solid catalyst in a transesterification, which covering is made by at least one of phosphorous, phosphorous compounds, calcium, and calcium compounds that are contained in fat and oil serving as a reaction raw material.

In order to subject fat and oil to a chemical reaction (such as transesterification), it is general to perform a degum process in which a gum component such as phospholipid and protein that is contained in fat and oil is removed, as described in Patent Document 8. The degum process is a conventional and well-known process. Specifically, the degum process is a process in which phosphorous acid, sulfuric acid, hydrochloric acid, boric acid, or citric acid and a gum component hydrated by adding water to fat and oil are removed by centrifugal separation. However, in the conventional degum process, it is impossible to completely remove phospholipid contained in the fat and oil or phosphorous or phosphorous compounds that has been mixed in other process, and consequently phosphorous atoms, i.e., approximately 5 ppm phosphorous or phosphorous compounds, remains in the fat and oil having been subjected to the degum process. Further, calcium atoms, i.e., approximately 2 ppm calcium or calcium compounds, also remains in the fat and oil having been subjected to the degum process.

That is, the inventors of the present invention have found that, in fat and oil having been subjected to only the conventional degum process, the surface of a solid catalyst is covered with at least one selected from phosphorous, phosphorous compounds, calcium, and calcium compounds, and consequently the solid catalyst deteriorates.

The present invention was completed based on the above finding, and includes the following subject matters.

The method of the present invention for producing fatty acid alkyl ester and/or glycerin includes a first reaction step of reacting fat and oil with alcohol over a solid catalyst; a first alcohol stripping step of evaporating, from a first reaction liquid obtained in the first reaction step, unreacted alcohol that remains without reacting in the first reaction step; and an alcohol refining step of refining the alcohol from the unreacted alcohol with use of at least a part of heat of the unreacted alcohol.

With the arrangement, at least a part of heat of the unreacted alcohol evaporated from the reaction liquid obtained in the first reaction step of reacting the fat and oil with the alcohol over a solid catalyst is used in the alcohol refining step of refining the alcohol from the unreacted alcohol.

Thus, at least a part of energy required in the alcohol refining step can be obtained from heat generated inside the reaction system. That is, it is possible to reduce the amount of energy to be produced outside the reaction system. This yields the effect that costs in producing fatty acid alkyl ester and glycerin over a solid catalyst can be reduced.

In the present specification etc., "reaction system" indicates a series of steps of producing fatty acid alkyl ester and/or glycerin from alcohol and fat and oil. That is, being "inside the reaction system" indicates being in a step of a series of steps of producing fatty acid alkyl ester and/or glycerin, and being "outside the reaction system" indicates being in a step other than a series of steps of producing fatty acid alkyl ester and/or glycerin.

It is preferable to arrange the method of the present invention so that at least two stages of pressures that are different from each other are applied in the first alcohol stripping step.

When at least two stages of pressures that are different from each other are applied in evaporating the unreacted alcohol from the reaction liquid, it is possible to effectively use heat of the unreacted alcohol as an energy source in the reaction system. This yields the effect of further reducing production costs in the method for producing fatty acid alkyl ester and/or glycerin over a solid catalyst.

It is preferable to arrange the method of the present invention so that a first stage of the pressures in the first alcohol stripping step ranges from 0.15 to 1.5 MPa.

When the first stage of the pressures in the first alcohol stripping step is within the range, it is possible to evaporate, from the reaction liquid obtained in the first reaction step, a large part of the unreacted alcohol contained in the reaction liquid. Further, it is possible to use heat of condensation of the evaporated unreacted alcohol as an energy source for the alcohol refining step.

It is preferable to arrange the method of the present invention to further include a second reaction step of reacting fat and oil with alcohol over a solid catalyst, the fat and oil being contained in an upper phase obtained by phase-separating refined products obtained in the first alcohol stripping step; and a second alcohol stripping step of evaporating, from a second reaction liquid obtained in the second reaction step, unreacted alcohol that remains without reacting in the second reaction step, in the alcohol refining step, the alcohol being refined from the unreacted alcohol evaporated in the first and second alcohol stripping steps, with use of at least a part of heat of the unreacted alcohol.

With the arrangement, at least a part of heat of the unreacted alcohol evaporated from the reaction liquid obtained in the second reaction step of reacting fat and oil with alcohol over a solid catalyst is used in the alcohol refining step, the fat and oil being contained in an upper phase obtained by phase-separating refined products obtained in the first alcohol stripping step.

This allows more amount of energy out of energy required in the production step to be obtained from heat generated within the reaction system. That is, it is possible to further reduce the amount of energy to be produced outside the reaction system. This allows further reducing production costs in producing fatty acid alkyl ester and/or glycerin over a solid catalyst.

It is preferable to arrange the method of the present invention so that at least two stages of pressures that are different from each other are applied in the second alcohol stripping step.

When at least two stages of pressures that are different from each other are applied in evaporating the unreacted alcohol from the reaction liquid, it is possible to effectively use heat of the unreacted alcohol as an energy source in the reaction system. This yields the effect of further reducing production costs in the method for producing fatty acid alkyl ester and/or glycerin over a solid catalyst.

It is preferable to arrange the method of the present invention so that a first stage of the pressures in the second alcohol stripping step ranges from 0.15 to 1.5 MPa.

When the first stage of the pressures in the second alcohol stripping step is within the range, it is possible to evaporate, from the reaction liquid obtained in the second reaction step, a large part of the unreacted alcohol contained in the reaction liquid. Further, it is possible to use heat of condensation of the evaporated unreacted alcohol as an energy source for the alcohol refining step.

It is preferable to arrange the method of the present invention so that a substance that is contained in the alcohol obtained in the alcohol refining step and that is other than the alcohol accounts for not more than 1000 ppm of all components contained in the alcohol obtained in the alcohol refining step.

When the substance that is contained in the alcohol and that is other than the alcohol is in the above range, it is possible to preferably use the refined alcohol as a raw material for the transesterification.

It is preferable to arrange the method of the present invention to further include a first phase-separation step of phase-separating the first reaction liquid obtained in the first reaction step into a first fatty acid alkyl ester phase and a first glycerin phase; a second reaction step of reacting fat and oil contained in the first fatty acid alkyl ester with alcohol over a solid catalyst; a third alcohol stripping step of evaporating, from a second reaction liquid obtained in the second reaction step, unreacted alcohol that remains without reacting in the second reaction step, with use of an evaporator including a heat exchanger selected from a thin film evaporator with an agitating rotor, a thin film evaporator with tubes arranged as a bundle, and a thin film evaporator with a centrifugal rotor; and a second phase-separation step of phase-separating refined products obtained in the third alcohol stripping step into a second fatty acid alkyl ester phase and a second glycerin phase.

With the arrangement, in the first reaction step, the fat and oil and the alcohol are caused to react with each other over a solid catalyst, thereby producing the first reaction liquid containing fatty acid alkyl ester, glycerin, unreacted fat and oil, unreacted alcohol, and a reaction intermediate such as glyceride. Then, in the first phase-separation step, the first reaction liquid is separated, thereby obtaining the first fatty acid alkyl ester phase containing fatty acid alkyl ester, unreacted fat and oil, unreacted alcohol, and the reaction intermediate, and the first glycerin phase containing glycerin and unreacted alcohol. Further, in the second reaction step, the first fatty acid alkyl ester phase and the alcohol are caused to react with each other, thereby obtaining the second reaction liquid containing fatty acid alkyl ester, glycerin, and unreacted alcohol.

Subsequently, in the alcohol stripping step, the unreacted alcohol is evaporated from the second reaction liquid with use of the evaporator including a heat exchanger with a short residence time. Finally, the refined products are phase-separated in the second phase-separation step, thereby obtaining the second fatty acid alkyl ester phase containing fatty acid alkyl ester and the second glycerin phase containing glycerin.

With the arrangement, in the third alcohol stripping step, the alcohol is evaporated with use of the evaporator including the heat exchanger with a short residence time. Consequently, it is possible to prevent excessively heating fatty acid alkyl ester and/or glycerin that is to be an end product, thereby preventing reverse reaction from proceeding. Further, since the alcohol is sufficiently removed from the materials (the refined products) to be phase-separated in the second phase-separation step, it is possible to prevent fatty acid alkyl ester from being distributed to the second glycerin phase, thereby preventing drop of the yield of fatty acid alkyl ester, and omitting refining after the phase-separation.

As described above, with the arrangement, it is possible to produce high-quality fatty acid alkyl ester and/or glycerin with high yield and with easiness.

Further, it is preferable to arrange the method so that the residence time is 20 minutes or less. When the residence time is 20 minutes or less, the above effect can be yielded.

It is preferable to arrange the method of the present invention so that in the third alcohol stripping step, the unreacted alcohol that remains without reacting in the first reaction step is further evaporated from the first glycerin phase with use of the evaporator.

With the arrangement, the alcohol can be evaporated from the second reaction liquid and the first glycerin phase with use of one evaporator. Here, the evaporator for evaporating the alcohol from the first glycerin phase may be the evaporator used in the steps in the above production method. With the arrangement, particularly in the evaporator for evaporating the alcohol from the second reaction liquid, the alcohol is evaporated from the first glycerin phase as well as from the second reaction liquid. An example of a method for evaporating the alcohol from the first glycerin phase is a method for evaporating alcohol before the first phase-separation step. In order to make alcohol concentration in glycerin not more than 1%, it is necessary to heat a reaction liquid containing fatty acid alkyl ester and glycerin for a long time. This causes reverse reaction in the transesterification, which is not preferable. Further, Patent Document 1 discloses a production method in which an evaporator for the second reaction liquid is not used for an evaporator for evaporating alcohol from the first glycerin phase. However, this requires providing an additional evaporator and an additional separator, which is not preferable.

Further, with the arrangement of the present invention, the alcohol is evaporating from the first glycerin phase with use of the evaporator. Consequently, when an end product is obtained from the first glycerin phase as well as from the second reaction liquid, it is possible to prevent excessive heating, thereby preventing reverse reaction. Further, it is possible to sufficiently remove the alcohol from the material to be phase-separated in the second phase-separation step, so that it is possible to prevent fatty acid alkyl ester from being distributed to the second glycerin phase, thereby preventing drop of the yield of fatty acid alkyl ester, and omitting refining after the phase-separation.

It is preferable to arrange the method of the present invention so that in the third alcohol stripping step, the unreacted alcohol that remains without reacting in the second reaction step is evaporated from the second reacting liquid obtained in the second reaction step, and the unreacted alcohol that remains without reacting in the first reaction step is evaporated from the first glycerin phase.

It is preferable to arrange the method of the present invention so that a second alcohol stripping step of evaporating unreacted alcohol from the second reaction liquid is performed before the third alcohol stripping step.

With the arrangement, before the third alcohol stripping step, the unreacted alcohol that remains without reacting in the second reaction step is evaporated from the second reaction liquid in the second reaction step. This reduces the amount of alcohol contained in a material to be evaporated in the third alcohol stripping step, thereby evaporating the unreacted alcohol with further higher efficiency.

It is preferable to arrange the method of the present invention so that the first alcohol stripping step is performed before the first phase-separation step.

With the arrangement, the amount of alcohol contained in a material to be evaporated in the third alcohol stripping step is reduced, thereby evaporating the unreacted alcohol with further higher efficiency.

It is preferable to arrange the method of the present invention so that in the third alcohol stripping step, the unreacted alcohol is evaporated in such a manner that the unreacted alcohol accounts for not more than 0.5 wt % of the refined products obtained in the third alcohol stripping step.

With the arrangement, the unreacted alcohol accounts for not more than 0.5 wt % of the refined products obtained in the alcohol stripping step, so that it is possible to prevent fatty acid alkyl ester from being distributed to the second glycerin phase, thereby preventing drop in the yield of fatty acid alkyl ester, and it is possible to omit refining after the phase-separation. Therefore, with the arrangement, it is possible to produce high-quality fatty acid alkyl ester and/or glycerin with high yield and with easiness.

It is preferable to arrange the method of the present invention so as to further include a removal step of removing at least one selected from phosphorous, phosphorous compounds, calcium, and calcium compounds that are contained in a reaction raw material including the fat and oil and the alcohol.

With the arrangement, at least one selected from phosphorous, phosphorous compounds, calcium, and calcium compounds that are contained in the reaction raw material is removed before the reaction step.

This allows preventing at least one selected from phosphorous, phosphorous compounds, calcium, and calcium compounds from covering the surface of the solid catalyst, so that it is possible to suppress drop of activity of the solid catalyst due to the covering by at least one selected from phosphorous, phosphorous compounds, calcium, and calcium compounds. In other words, it is possible to lengthen the life of the solid catalyst.

Further, by suppressing drop of activity of the solid catalyst, it is possible to reduce frequency of troublesome exchanging of a solid catalyst with dropped activity in producing fatty acid alkyl ester and/or glycerin.

Further, since the life of the solid catalyst is lengthened, it is possible to increase the amount of fatty acid alkyl ester and/or glycerin generated with respect to the same amount of the solid catalyst. This allows reducing the cost for the solid catalyst with respect to each product, and increasing productivity of fatty acid alkyl ester and/or glycerin.

It is preferable to arrange the method of the present invention so that in the removal step, at least one selected from phosphorous, phosphorous compounds, calcium, and calcium compounds is adsorbed and removed by an adsorber.

With the arrangement, it is possible to effectively remove at least one selected from phosphorous, phosphorous compounds, calcium, and calcium compounds.

It is preferable to arrange the method of the present invention so that in the removal step, concentration of phosphorous atoms in phosphorous and phosphorous compounds contained in the reaction raw material is less than 2.5 ppm.

By setting the concentration of phosphorous atoms in phosphorous and phosphorous compounds contained in the fat and oil and the alcohol in the reaction step to be in the above range, it is possible to further prevent covering of the surface of the solid catalyst by phosphorous and/or phosphorous compounds.

It is preferable to arrange the method of the present invention so that in the removal step, concentration of calcium atoms in calcium and calcium compounds contained in the reaction raw material is less than 1 ppm.

By setting the concentration of calcium atoms in calcium and calcium compounds contained in the fat and oil and the alcohol in the reaction step to be in the above range, it is possible to further prevent covering of the surface of the solid catalyst by calcium and/or calcium compounds.

It is preferable to arrange the method of the present invention so as to further include a first phase-separation step of phase-separating refined products into a first fatty acid alkyl ester phase and a first glycerin phase with use of a separation filter which is so called coalescer, the refined product being obtained by evaporating the unreacted alcohol from the first reaction liquid in the first alcohol stripping step; a second reaction step of reacting fat and oil contained in the first fatty acid alkyl ester phase with alcohol over a solid catalyst; and a second phase-separation step of phase-separating a second reaction liquid obtained in the second reaction step into a second fatty acid alkyl ester phase and a second glycerin phase with use of a separation filter.

With the arrangement, it is possible to very promptly and sufficiently perform phase-separation between the upper phase and the lower phase. This allows increasing the yield of fatty acid alkyl ester that is an end product, and lengthening the life of the solid catalyst used in the second reaction step.

In order to solve the foregoing problem, the device of the present invention for producing fatty acid alkyl ester and/or glycerin includes: a reactor for reacting fat and oil with alcohol over a solid catalyst; a stripper for stripping, from a reaction liquid obtained in the reactor, unreacted alcohol that remains without reacting in the reactor; and a refiner for refining the alcohol from the unreacted alcohol stripped in the stripper, with use of at least a part of heat of the unreacted alcohol.

It is preferable to arrange the device of the present invention to further include a packed device filled with an adsorber for adsorbing at least one selected from phosphorous, phosphorous compounds, calcium, and calcium compounds that are contained in a reaction raw material including the fat and oil and the alcohol, the reactor causing the reaction raw material having passed the packed device to react over a solid catalyst.

Additional objects, features, and strengths of the present invention will be made clear by the description below. Further, the advantages of the present invention will be evident from the following explanation in reference to the drawings.

REFERENCE NUMERALS

Figure 1:
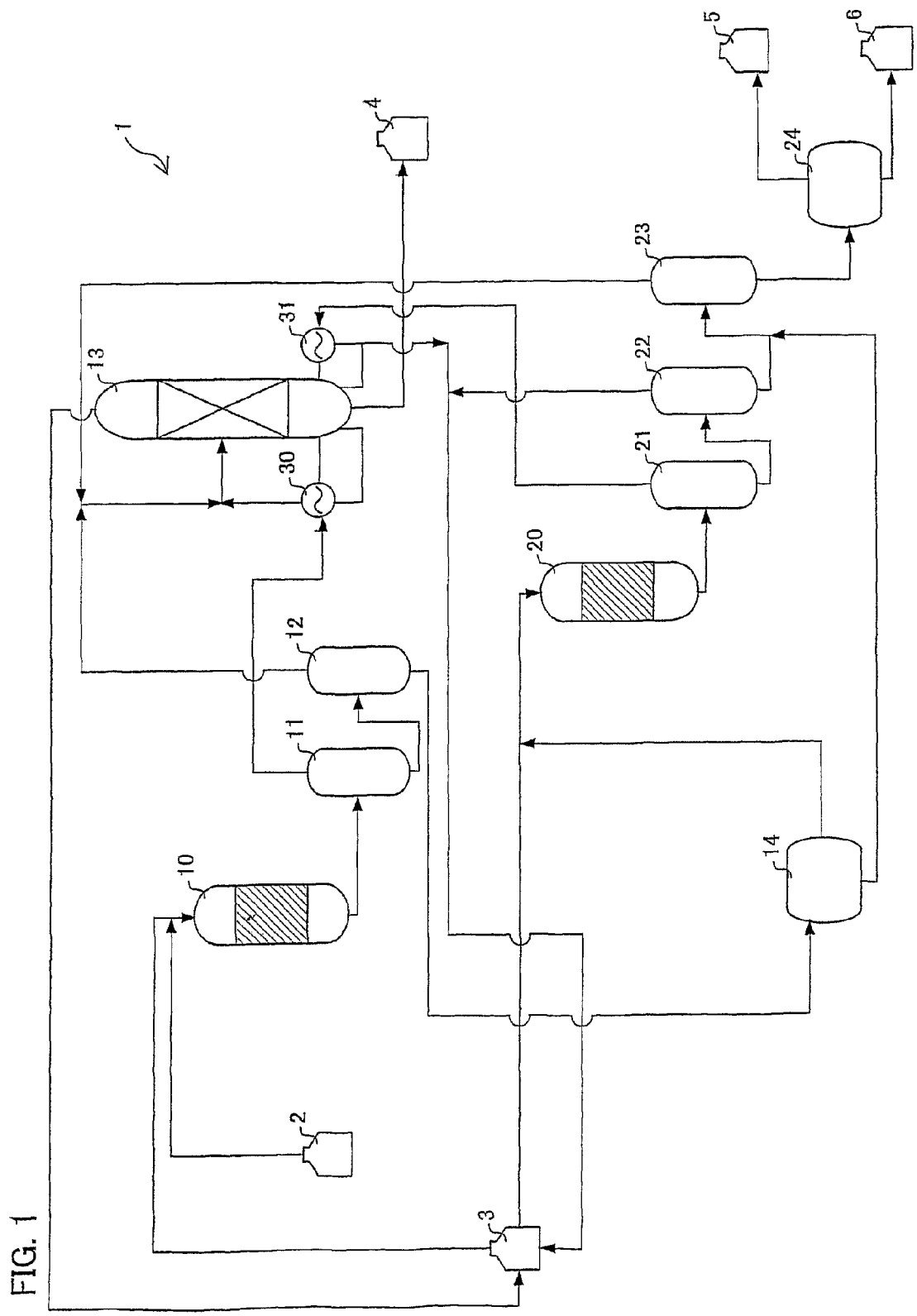
FIG. 1 is a drawing schematically illustrating a device for producing fatty acid alkyl ester and/or glycerin.

1. Production device
2. Fat and oil storage tank
3. Alcohol storage tank
4. Waste storage tank
5. Fatty acid alkyl ester storage tank
6. Glycerin storage tank
10. First reactor
11. First high pressure flash tower
12. First low pressure flash tower
13. Alcohol refining tower
14. First phase separator
20. Second reactor
21. Second high pressure flash tower
22. Second low pressure flash tower
23. Alcohol evaporator
24. Second phase separator
25. Packed device
29. Solid-liquid separator
30, 31. Heat exchanger

BEST MODE FOR CARRYING OUT THE INVENTION

A method for producing fatty acid alkyl ester and/or glycerin is described below in accordance with an embodiment of the present invention. "Fatty acid alkyl ester and/or glycerin" in the present specification etc. is synonymous with "at least one of fatty acid alkyl ester and glycerin."

The method of the present embodiment for producing fatty acid alkyl ester and/or glycerin mainly includes a first reaction step, a second reaction step, a first phase-separation step, a second phase-separation step, a first alcohol stripping step, a second alcohol stripping step, a third alcohol stripping step, an alcohol refining step, a removal step, and a solid-liquid separating step. These steps are detailed later.

(Process for Producing Fatty Acid Alkyl Ester and/or Glycerin)

With reference to FIG. 1, the following explains a process for producing fatty acid alkyl ester and/or glycerin, including the above steps. FIG. 1 is a drawing schematically illustrating a production device of the present invention for producing fatty acid alkyl ester and/or glycerin.

As illustrated in FIG. 1, a production device 1 for producing fatty acid alkyl ester and/or glycerin mainly includes a fat and oil storage tank 2, alcohol storage tank 3, a waste storage tank 4, a fatty acid alkyl ester storage tank 5, a glycerin storage tank 6, a first reactor 10, a first high pressure flash tower 11, a first low pressure flash tower 12, an alcohol refining tower 13, a first phase separator 14, a second reactor 20, a second high pressure flash tower 21, a second low pressure flash tower 22, an alcohol evaporator 23, a second phase separator 24, a heat exchanger 30, a heat exchanger 31, and lines connecting these members.

As illustrated in FIG. 1, alcohol is supplied from the alcohol storage tank 3 to the first reactor 10, and fat and oil are supplied from the fat and oil storage tank 2 to the first reactor 10. In this process, the fat and oil and the alcohol are heated and pressured before being supplied to the first reactor 10 filled with a solid catalyst. The first reactor 10 and the first reaction step in the first reactor 10 are detailed later.

A first reaction liquid containing fatty acid alkyl ester, glycerin, unreacted part of the above fat and oil, unreacted part of the above alcohol, and a reaction intermediate such as glyceride is obtained by passing the first reactor 10 and is supplied to the first high pressure flash tower 11. The first high pressure flash tower 11 evaporates the unreacted alcohol from the first reaction liquid, and the evaporated unreacted alcohol is supplied to the heat exchanger 30. The reaction liquid from which the unreacted alcohol has been evaporated is supplied to the first low pressure flash tower 12. The first low pressure flash tower 12 evaporates the unreacted alcohol from the first reaction liquid, and the evaporated unreacted alcohol is supplied to the alcohol refining tower 13. The reaction liquid from which the unreacted alcohol has been evaporated in the first low pressure flash tower 12 is supplied to the first phase separator 14. The first alcohol stripping step in the first high pressure flash tower 11 and the first low pressure flash tower 12 are detailed later.

Subsequently, the heat exchanger 30 recovers heat of the unreacted alcohol supplied thereto, and the unreacted alcohol from which the heat has been recovered is supplied to the alcohol refining tower 13. The alcohol refining tower 13 refines alcohol from the unreacted alcohol with use of the heat having been recovered from the unreacted alcohol in the heat exchanger 30. The refined alcohol is supplied to the alcohol storage tank 3 and is reused as a raw material. Further, a waste liquid containing components other than the alcohol is exhausted from the production device and is stored in the waste storage tank 4. The heat exchanger 30 and the alcohol refining tower 13 and the alcohol refining step in the alcohol refining tower 13 are detailed later.

On the other hand, the reaction liquid from which the unreacted alcohol has been evaporated is supplied to the first phase separator 14 and is phase-separated by the first phase separator 14 into a fatty acid alkyl ester phase (upper phase, hydrophobic phase) and a glycerin phase (lower phase, hydrophilic phase) (first phase-separation step). A first fatty acid alkyl ester phase in the upper phase is mixed with alcohol supplied from the alcohol storage tank 3 and is supplied to the second reactor 20. Thus, unreacted fat and oil contained in the fatty acid alkyl ester phase are completely reacted. The second reactor 20 and the second reaction step in the second reactor 20 are detailed later.

A second reaction liquid containing fatty acid alkyl ester, glycerin, and unreacted alcohol is obtained by passing the second reactor 20 and is supplied to the second high pressure flash tower 21. The second high pressure flash tower 21 evaporates the unreacted alcohol from the second reaction liquid, and the evaporated unreacted alcohol is supplied to the heat exchanger 31. The second reaction liquid from which the unreacted alcohol is evaporated is supplied to the second low pressure flash tower 22. The second low pressure flash tower 22 evaporates the unreacted alcohol contained in the reaction liquid, and the evaporated unreacted alcohol is supplied to the alcohol storage tank 3 and reused as a raw material. The second reaction liquid from which the unreacted alcohol has been removed in the second low pressure flash tower 22 is supplied to the alcohol evaporator 23. The second alcohol stripping step in the second high pressure flash tower 21 and the second low pressure flash tower 22 is detailed later.

Subsequently, the heat exchanger 31 recovers heat of the unreacted alcohol supplied thereto, and the unreacted alcohol from which the heat has been recovered is supplied to the alcohol storage tank 3. On the other hand, the second reaction liquid from which the unreacted alcohol has been evaporated and the first glycerin contained in the glycerin phase separated by the first phase separator 14 are supplied to the alcohol evaporator 23, and unreacted alcohol contained in the supplied second reaction liquid and in the supplied glycerin is further evaporated by the alcohol evaporator 23. The evaporated unreacted alcohol is supplied to the alcohol refining tower 13 and reused as alcohol.

A refined product obtained by evaporating the unreacted alcohol from the second reaction liquid and the lower phase obtained in the first phase-separation step (first glycerin phase) in the alcohol evaporator 23 is supplied to the second phase separator 24. The second phase separator 24 phase-separates the supplied refined product into a fatty acid alkyl ester phase (upper phase, hydrophobic phase) and a glycerin phase (lower phase, hydrophilic phase). The second fatty acid alkyl ester phase that is the upper phase is supplied to the fatty acid alkyl ester storage tank 5, and the second glycerin phase that is the lower phase is supplied to the glycerin storage tank 6.

Note that a series of steps in a "reaction system" refer to the whole of a series of the above process steps. That is, all of process steps other than the above process steps are outside the "reaction system."

(Details of First Reaction Step and Second Reaction Step)

The following details the first reaction step and the second reaction step. Each of the first and second reaction steps is a step of generating fatty acid alkyl ester and/or glycerin by mixing a fat and oil with alcohol and subjecting the mixture to a transesterification over a solid catalyst.

In the transesterification, it is possible to simultaneously obtain fatty acid alkyl ester and glycerin, and therefore it is possible to industrially and easily obtain refined glycerin useful as a chemical material for various purposes and fatty acid alkyl ester useful for a biodiesel fuel. Solid catalysts, alcohols, and fats and oils that may be preferably used in the present invention are detailed later.

A temperature of a mixture solution of the fat and oil and the alcohol in the first reactor 10 and the second reactor 20, i.e., a reaction temperature preferably ranges from 100 to 300° C., more preferably ranges from 120 to 270° C., and further preferably ranges from 150 to 235° C. When the reaction temperature is within the above range, it is possible to sufficiently increase a reaction speed and to sufficiently prevent decomposition of the alcohol.

Pressures in the first reactor 10 and the second reactor 20, i.e., reaction pressures preferably range from 0.1 to 10 MPa, more preferably range from 0.2 to 9 MPa, and further preferably range from 0.3 to 8 MPa. When the reaction pressure is within the above range, it is possible to sufficiently increase the reaction speed and to sufficiently prevent a side reaction. When the reaction pressure exceeds 10 MPa, a special device resistible under a high pressure is required and therefore additional costs such as equipment costs are required.

The amounts of the alcohol and the amount of the fat and oil that are to be supplied to the first reactor 10 and the second reactor 20 are such that the amount of the alcohol relative to the amount of the fat and oil preferably range from 1 to 30 times larger than the theoretically required amount, more preferably range from 1.2 to 20 times larger than the theoretically required amount, and still more preferably range from 1.5 to 15 times larger than the theoretically required amount, and further preferably range from 2 to 10 times larger than the theoretically required amount. When the amount of the alcohol relative to the amount of the fat and oil is within the range, it is possible to cause the fat and oil and the alcohol to sufficiently react with each other, and to sufficiently increase a conversion rate of the fat and oil. Further, it is possible to reduce the amount of the collected alcohol in the first alcohol stripping step or the second alcohol stripping step and to reduce utility costs necessary for the alcohol refining tower 13 or the alcohol evaporator 23, so that it is possible to reduce production costs.

The theoretically required amount of alcohol in the present specification etc. refers to the number of moles of the alcohol with respect to a saponification value of a fat and oil, and is calculated in accordance with the following equation.

Theoretically required amount of alcohol (g)=amount of molecules of alcohol×[amount of used fat and oil (g)×saponification value (mg (KOH)/g (fat and oil)/56100)

The shape of each of the first reactor 10 and the second reactor 20 may be either a batch type or a fixed bed flow type. However, it is preferable that the shape is a fixed bed flow type. When each of the first reactor 10 and the second reactor 20 is a fixed bed reaction device filled with a solid catalyst, a step for separating a catalyst is unnecessary. This allows omitting a troublesome work, making industrial production easier. When each of the first reactor 10 and the second reactor 20 is a fixed bed reaction device or a batch reaction tank, conditions such as a reaction time may be conventional and well-known conditions.

In a case where the fat and oil contain impurities such as phospholipid and protein, there may be provided a degumming reaction tank for performing a degumming process in which the impurities are removed by adding mineral acid. It is preferable that the degumming reaction tank is provided at a stage prior to the first reactor 10. It is more preferable that the degumming reaction tank is provided at a stage prior to the mixing of the fat and oil with the alcohol.

(Details of the First and Second Alcohol Stripping Steps)

The following details the first and second alcohol stripping steps. The first and second alcohol stripping steps are steps of evaporating unreacted alcohols from the reaction liquids obtained in the first and second reaction steps, respectively.

It is preferable that each of the first and second alcohol stripping steps is performed with at least two stages of pressures that are different from each other. With reference to FIG. 1, a refinement at the first stage is a refinement in the first high pressure flash tower 11 or the second high pressure flash tower 21, and a refinement at the second stage is a refinement in the first low pressure flash tower 12 or the second low pressure flash tower 22.

A pressure of the refinement at the first stage in the first and second alcohol stripping steps, i.e., a pressure of the first high pressure flash tower 11 or the second high pressure flash tower 21 preferably ranges from 0.15 to 1.5 MPa, and more preferably ranges from 0.20 to 1.0 MPa. Further, it is preferable that a pressure of the first low pressure flash tower 12 or the second low pressure flash tower 22 is a normal pressure.

"Normal pressure" in the present specification etc. means a pressure ranging from 0.095 to 0.105 MPa.

When the pressure at the first stage in the first and second alcohol stripping steps is within the above range, the unreacted alcohol contained in the reaction liquid can be sufficiently evaporated. Further, when the pressure at the first stage in the first and second alcohol stripping steps is within the above range, it is possible to collect the unreacted alcohol at a temperature higher than a boiling point (at a normal pressure). Thus, heat of condensation of the unreacted alcohol can be used in the alcohol refining step.

In the present embodiment, each of the first and second alcohol stripping steps is refinement with two stages. However, the present invention is not limited to this, and each of the first and second alcohol stripping steps may be refinement with one stage or refinement with three or more stages.

However, each of the first and second alcohol stripping steps is preferably refinement with two or more stages, since this case allows effectively using heat of the unreacted alcohol as an energy source inside the reaction system. For example, in the case where each of the first and second alcohol stripping steps is refinement with two stages, the heat of the unreacted alcohol evaporated in the normal pressure flash tower 12 and/or the normal pressure flash tower 22 can be used as an energy source for increasing a temperature of fat and oil and/or alcohol.

In a case where the first alcohol stripping step and/or the second alcohol stripping step is refinement with one stage in the pressure flash tower, the amount of alcohol contained in a heavy liquid extracted from the bottom of the pressure flash tower is large, which may worsen a separation efficiency in the phase-separation step that is a next step. Specifically, there is a possibility that fatty acid alkyl ester and/or monoglyceride is distributed to the glycerin phase, and the yield and the purity of fatty acid alkyl ester and/or glycerin drop.

In FIG. 1, the heat of the unreacted alcohol evaporated in the first high pressure flash tower 11 and the second high pressure flash tower 21 is used in the alcohol refining step. However, the present invention is not limited to this. Only the heat of the unreacted alcohol evaporated in one of the first high pressure flash tower 11 and the second high pressure flash tower 21 may be used in the alcohol refining step.

The first high pressure flash tower 11, the second high pressure flash tower 21, the first low pressure flash tower 12, and the second low pressure flash tower 22 may be conventional and well known flash towers.

(Detail of the Alcohol Refining Step)

The following details the alcohol refining step. The alcohol refining step is carried out in the alcohol refining tower 13. The alcohol refining step is a step of refining unreacted alcohol into alcohol that can be reused as a raw material for the first and second reaction steps. "Refining" in the present specification etc. means a refining unreacted alcohol into alcohol that can be used as a raw material in the reaction step.

To be more specific, the alcohol refining tower 13 used in the alcohol refining step is provided with the heat exchangers 30 and 31 at its bottom, and evaporates the unreacted alcohol with use of energy recovered in the heat exchangers 30 and 31 so as to obtain a refined alcohol.

Contaminants contained in the unreacted alcohol are mainly water. In a case where the alcohol to be refined has a boiling water lower than that of water, the refined alcohol is obtained as gas from the upper part of the alcohol refining tower 13, and wastes having a boiling point higher than the alcohol, such as water, are extracted from the lower part of the alcohol refining tower 13 and are supplied to the waste storage tank 4. In a case where the alcohol to be refined has a boiling point higher than that of water, the refined alcohol is extracted from the lower part of the alcohol refining tower 13 and wastes having a boiling point lower than that of the alcohol are exhausted as gas from the upper part of the alcohol refining tower 13.

In a case where the alcohol obtained by refinement in the alcohol refining step is reused as a raw material, concentration of water included in the alcohol is preferably not more than 1000 ppm, more preferably not more than 700 ppm, and further preferably not more than 500 ppm. This is because water contained in the alcohol causes hydrolysis of fatty acid alkyl ester to proceed in the reaction step, making the yield of the fatty acid alkyl ester lower.

When the concentration of water in the alcohol is within the above range, it is possible to prevent decrease of catalytic ability and elution of active ingredient that are caused by fatty acid derived from hydrolysis of fatty acid alkyl ester, so that is it possible to use a catalyst for a long time.

The heat exchangers 30 and 31 are not particularly limited. However, the heat exchangers 30 and 31 are preferably heat exchangers of a gas-liquid contact type, since the unreacted alcohols obtained in the first and second alcohol stripping steps are gas. That is, it is preferable that heat generated when condensing the unreacted alcohols obtained in the first and second alcohol stripping steps is recovered in the heat exchanger 30 or 31 and used as a heat source in the alcohol refining tower 13.

To be more specific, the heat exchangers 30 and 31 cause the unreacted alcohols that are obtained as gas in the first and second alcohol stripping steps to contact with unreacted alcohol in a liquid to be refined, thereby recovering heat from the unreacted alcohols in the gas form. Subsequently, the heat recovered from the unreacted alcohols in the gas form is used as energy for refining the unreacted alcohol in the liquid, i.e., energy used in the alcohol refining step. The unreacted alcohols from which the heat has been recovered and which have changed from gas to a liquid may be supplied to the alcohol refining tower 13 so as to be unreacted alcohol to be refined.

The liquid which the unreacted alcohols in the gas form is to contact with is not limited to the unreacted alcohol in the liquid to be refined, and may be other liquid.

(Detail of the Third Alcohol Stripping Step)

The third alcohol stripping step carried out in the alcohol evaporator 23 is a step of removing alcohol from the second reaction liquid and the first glycerin phase before phase-separating the second reaction liquid and the first glycerin phase and obtaining an end product (fatty acid alkyl ester and/or glycerin).

The alcohol evaporator 23 is an evaporator provided with a heat exchanger (heater) with a short residence time. Specific examples thereof include a thin film evaporator with an agitating rotor (e.g. wiped film evaporator), with tubes arranged as a bundle (e.g. falling film evaporator, climbing film evaporator), and with a centrifugal rotor (centrifugal thin film evaporator).

The residence time is preferably within 20 minutes, and more preferably within 10 minutes. When the residence time is long, a reverse reaction of the transesterification occurs depending on a temperature of a heater, which decreases the yield of fatty acid alkyl ester, accompanied by decrease in purity of a refined product.

The temperature of the heater in the third alcohol stripping step is preferably not more than 250° C., and more preferably not more than 200° C. When the temperature of the heater exceeds 250° C., the reverse reaction of the transesterification occurs within an extremely short time, which is not preferable. For example, a time necessary for 0.1 mol % of fatty acid alkyl ester to decompose due to the reverse reaction is 35 minutes at 150° C., 10 minutes at 200° C., and 4 minutes at 250° C.

The pressure in the third alcohol stripping step ranges preferably from 0.012 to 0.090 MPa, more preferably from 0.020 to 0.050 MPa. When the pressure is within the above range, evaporation can be performed at a temperature where the reverse reaction of the transesterification hardly occurs, and it is unnecessary to provide a cooling device for condensing alcohol.

In the third alcohol stripping step, by using the alcohol evaporator 23 with the above arrangement, it is possible to sufficiently evaporate and remove a small amount of alcohols from the second reaction liquid and the first glycerin phase without subjecting the second reaction liquid and the first glycerin phase to excessive heat history. Consequently, it is possible to prevent a phenomenon that fatty acid alkyl ester and/or glycerin that is to be an end product is heated excessively and a reverse reaction proceeds. Further, since the unreacted alcohol is sufficiently removed before the second phase-separation step, it is possible to prevent a phenomenon that fatty acid alkyl ester is distributed to the second glycerin phase in the second phase-separation step and the yield of fatty acid alkyl ester drops. Further, since it is possible to reduce the amount of alcohol in the second fatty acid alkyl ester phase and the second glycerin phase that are obtained in the second phase-separation step, it is unnecessary to perform refinement after the second phase-separation step.

As described above, in the method of the present embodiment for producing fatty acid alkyl ester and/or glycerin, the unreacted alcohol in the second reaction liquid is evaporated in the second alcohol stripping step. Further, the first glycerin phase is obtained by phase-separating the first reaction liquid from which the unreacted alcohol has been evaporated in the first alcohol stripping step. Consequently, the second reaction liquid and the first glycerin phase from both of which alcohol is to be removed in the third alcohol stripping step have small amount of unreacted alcohol. Therefore, in the third alcohol stripping step, it is only necessary to evaporate and remove a small amount of alcohol contained in the second reaction liquid and the first glycerin phase. This allows further reducing the alcohol content in a resulting refined product.

Specifically, in the third alcohol stripping step, refinement is performed so that the alcohol content in the resulting refined product is more preferably not more than 0.5 wt %, still more preferably not more than 0.3 wt %, and further more preferably not more than 0.2 wt %.

As described above, in the present embodiment, the alcohol content in the refined product is very low, so that it is possible to increase the yield of fatty acid alkyl ester and to omit a refinement process after the second phase-separation step.

In the present embodiment, the first glycerin phase is evaporated in the alcohol evaporator 23. However, the present invention is not limited to this, and the first glycerin phase may be evaporated in other evaporator. However, in that case, there is a possibility that unreacted alcohol is not sufficiently evaporated from the first glycerin phase. Further, in a case where an already existing alcohol evaporator is not used, additional costs may be required. However, even in such a case, the present invention is designed so that at least the second reaction liquid is evaporated in the evaporator, and therefore the present invention yields the above effect.

(First Phase Separator 14 and Second Phase Separator 24)

The first phase separator 14 and the second phase separator 24 may be continuous gravity settlers, but are preferably coalescers, or are combination of them. A coalescer is a device for separating a mixture of immiscible liquids, wherein the mixture comprises a discontinuous liquid phase that is dispersed in a continuous liquid phase, by contacted with a coalescing medium to cause the dispersed phase to merge into larger droplets which then separate from the continuous phase on the basis of density. This allows very swift phase-separation between an upper phase and a lower phase with sureness. Consequently, it is possible to obtain both the upper phase and the lower phase with high purity in a short time.

A transesterification between fat and oil and alcohol is an equilibrium reaction. Consequently, when glycerin is dispersed or finely dispersed in the upper phase (fatty acid alkyl ester phase) that has been phase-separated in the first phase separator 14, a reaction in the second reaction step is disadvantageous in terms of equilibrium, and therefore unconverted glycerides are likely to remain.

The first phase separator 14 performs phase-separation with use of a coalescer, thereby preventing glycerin from being dispersed or finely dispersed in the upper phase. This increases the yield of fatty acid alkyl ester that is an end product.

In the reaction for generating fatty acid alkyl ester and glycerin in the present embodiment, there is a case where water is produced as a by-product in the reaction step. When water produced as a by-product in the first reaction step is supplied along with the upper phase (fatty acid alkyl ester phase) to the second reactor 20 in the second reaction step that is a subsequent stage, the water may cause deterioration of a solid catalyst and by-production of free fatty acid. However, since the water is distributed to the lower phase (glycerin phase) in the phase-separation step, the deterioration of the solid catalyst and the by-production of the free fatty acid do not occur when the upper phase and the lower phase are surely phase-separated.

Therefore, when the first phase separator 14 performs phase-separation with use of a coalescer, it is possible to increase the yield of fatty acid alkyl ester that is an end product, and to lengthen the life of the solid catalyst in the second reactor 20.

(Addition)

In order to obtain fatty acid alkyl ester and/or glycerin each with further higher purity in the first phase separator 14 and the second phase separator 24, there may be additionally provided a refining tower in a stage subsequent to the first phase separator 14 and the second phase separator 24.

A part of heat obtained in the first alcohol stripping step or the second alcohol stripping step may be used as an energy source in the alcohol evaporator 23.

(Detail of Removal Step)

Figure 2:
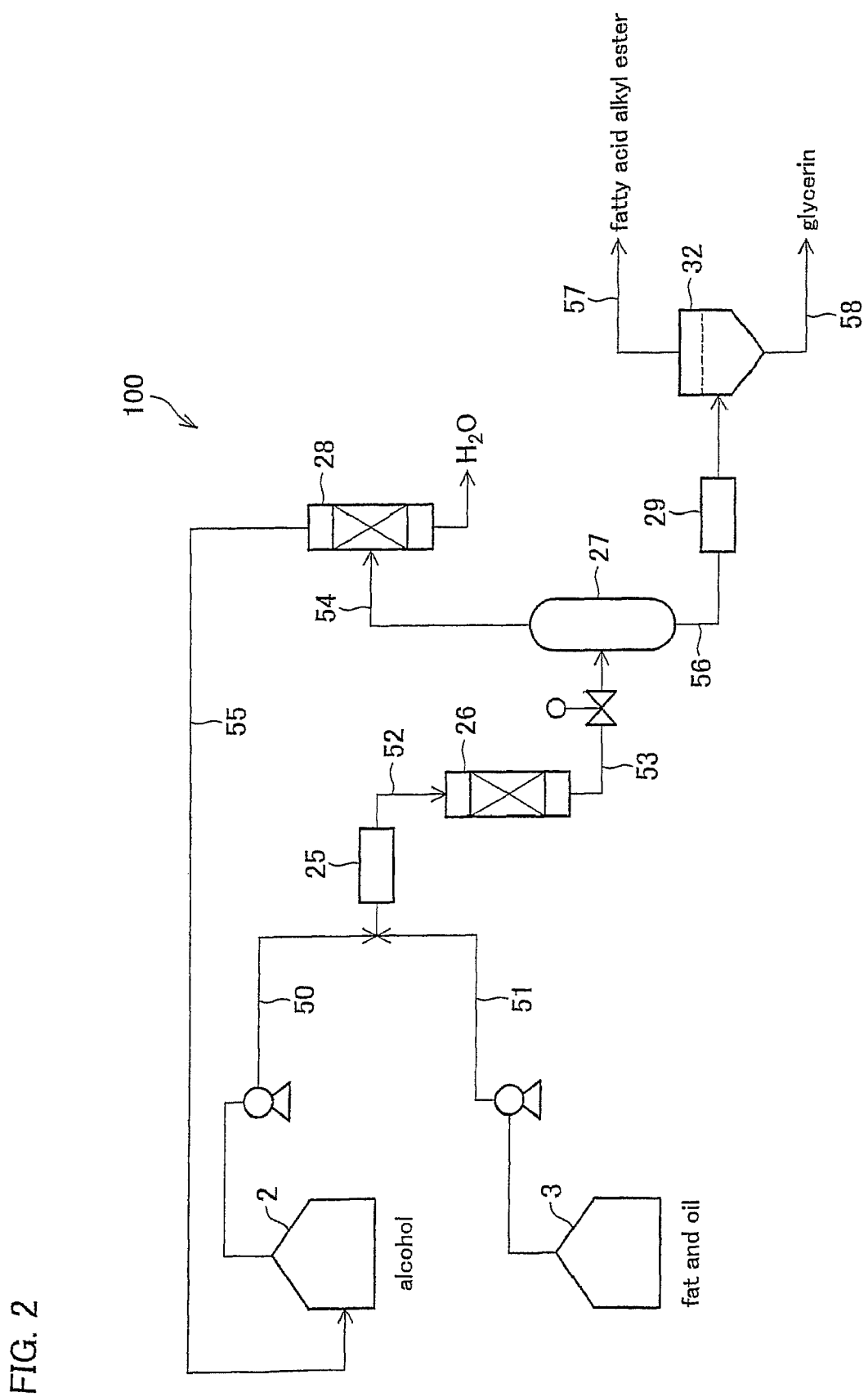
FIG. 2 is a drawing schematically illustrating a device for producing fatty acid alkyl ester and/or glycerin.

An explanation is made as to the removal step with reference to FIG. 2. FIG. 2 is a block diagram schematically illustrating a production device.

As illustrated in FIG. 2, a production device 1 for producing fatty acid alkyl ester and/or glycerin includes an alcohol storage tank 2, a fat and oil storage tank 3, a packed device 25, a reactor 26, an alcohol stripping tower 27, an alcohol refining tower 28, a solid-liquid separator 29, and a phase separator 32. The reactor 26 corresponds to the first reactor 10 in FIG. 1, the alcohol stripping tower 27 corresponds to the first high pressure flash tower 11 and the first low pressure flash tower 12 in FIG. 1, the alcohol refining tower 28 corresponds to the alcohol refining tower 13 in FIG. 1, and the phase separator 32 corresponds to the first phase separator 14 in FIG. 1.

The alcohol storage tank 2 is a tank in which alcohols are stored, and the fat and oil storage tank 3 is a tank in which fats and oils are stored. The alcohol storage tank 2 and the fat and oil storage tank 3 are connected with lines 50 and 51, respectively, and the lines 50 and 51 are connected with a line 52 that is connected with the upper side of the reactor 26 (the end of the reactor 26 to which end a reaction material is supplied). That is, the alcohol storage tank 2 is connected with the line 52 via the line 50, and the fat and oil storage tank 3 is connected with the line 52 via the line 51.

The line 52 is provided with the packed device 25, and a mixture of alcohols and fats and oils is supplied to the reactor 26 via the packed device 25. The reactor 26 is connected with the alcohol stripping tower 27 via the line 53, the alcohol stripping tower 27 is connected with the alcohol refining tower 28 via the line 54, and the alcohol stripping tower 27 is connected with the phase separator 32 via the line 56. The line 56 is provided with the solid-liquid separator 29, and a reaction liquid from the alcohol stripping tower 27 is supplied to the phase separator 32 via the solid-liquid separator 29.

The alcohol refining tower 28 is connected with the alcohol storage tank 2 via the line 55. Alcohol collected in the alcohol refining tower 28 goes back to the alcohol storage tank 2 via the line 55 and is reused as a reaction material.

The removal step is a step of removing at least one of phosphorous, phosphorous compounds, calcium, and calcium compounds from a reaction material including fats and oils and alcohols through an adsorption process. That is, the removal step is a step of reducing phosphorous, phosphorous compounds, calcium, or calcium compounds that is included in the reaction material.

As illustrated in FIG. 2, the removal step is performed in the packed device 25 connected with the alcohol storage tank 2 and the fat and oil storage tank 3 via the lines 50 and 51, respectively.

The packed device 25 has a hollow shape, and is filled with an adsorber that adsorbs at least one of phosphorous, phosphorous compounds, calcium, and calcium compounds. Consequently, phosphorous, calcium and compounds thereof contained in a mixture liquid including the fat and oil and the alcohol that is introduced into the packed device 25 are removed by the adsorber that fills the packed device 25. The adsorber that fills the packed device 25 is not particularly limited as long as the adsorber adsorbs at least one of phosphorous, phosphorous compounds, calcium, and calcium compounds. Specific examples of the adsorber include silica, alumina, silica-alumina, activated clay, diatomite, titania, zirconia, iron oxide, hydrotalcite, and activated carbon. Among them, silica, alumina, silica-alumina, titania, zirconia, and activated carbon are more preferable.

In the present specification etc., concentration of phosphorous atoms (which may be also referred to as "phosphorous concentration" hereinafter) and concentration of calcium atoms (which may be also referred to as "calcium concentration" hereinafter) are obtained through an Inductively Coupled Plasma Mass Spectrometer (ICP-MS).

In the removal step, phosphorous concentration in the reaction material including the fat and oil and the alcohol is preferably less than 2.5 ppm, more preferably less than 2 ppm, and still more preferably less than 1.5 ppm. Further, calcium concentration in the reaction material including the fat and oil and the alcohol is preferably less than 1 ppm, more preferably less than 0.8 ppm, and still more preferably less than 0.5 ppm, and most preferably less than 0.2 ppm. When the phosphorous concentration is at least less than 2.5 ppm and the calcium concentration is at least less than 1 ppm in the reaction material including the fat and oil and the alcohol, it is possible to reduce the amount of the surface of the solid catalyst covered by at least one of phosphorous, phosphorous compounds, calcium, and calcium compounds in the later reaction step. This allows slowing decrease in activity of the solid catalyst due to covering by at least one of phosphorous, phosphorous compounds, calcium, and calcium compounds. That is, this allows lengthening the life of the solid catalyst.

Further, when the life of the solid catalyst is lengthened, frequency of catalyst exchange is decreased, and labor required for catalyst exchange can be reduced. Further, since it is possible to increase the amount of fatty acid alkyl ester and/or glycerin produced with respect to the same amount of the solid catalyst, it is possible to reduce costs for the solid catalyst with respect to each product, which allows increasing productivity of fatty acid alkyl ester and/or glycerin.

In FIG. 2, the packed device 25 is positioned at a point after the lines 50 and 51 have joined. However, the position of the packed device 25 is not limited to this as long as the packed device 25 is positioned at a point before the transesterification. That is, the packed device 25 may be positioned on the lines 50 and 51, may be positioned at an entrance of the reactor 26 (supply port for the reaction material) as explained below, or may be positioned to be integral with the fat and oil storage tank 2 and the alcohol storage tank 3. Further, the packed device 25 may be positioned at a point before the fat and oil storage tank 2 and the alcohol storage tank 3 so that the fat and oil and the alcohol are supplied to respective storage tanks while meeting at least one of two conditions, i.e., a condition that the total of phosphorous concentration is less than 2.5 ppm in the reaction and a condition that the total of calcium concentration is less than 1 ppm in the reaction.

As described above, the amounts of phosphorous, phosphorous compounds, calcium, and calcium compounds are so little that they may be ignored. Therefore, the present invention may be arranged so that only the phosphorous concentration and the calcium concentration in the fat and oil are reduced in order that the phosphorous concentration and the calcium concentration in the reaction material including the fat and oil and the alcohol are less than 2.5 ppm and less than 1 ppm, respectively.

Further, it is preferable that a plurality of the packed devices 25 are arrayed in parallel with respect to a direction in which the material is supplied. Consequently, while an adsorber in one packed device is replaced, it is possible to remove at least one of phosphorous, phosphorous compounds, calcium, and calcium compounds with use of other packed device that is not replaced. This allows replacement of an adsorber in the packed device without stopping an operation of the production device, i.e., without stopping production of fatty acid alkyl ester and/or glycerin. This prevents deterioration in productivity of fatty acid alkyl ester and/or glycerin.

The removal of at least one of phosphorous, phosphorous compounds, calcium, and calcium compounds is not necessarily performed by the packed device 25 as long as at least one of phosphorous, phosphorous compounds, calcium, and calcium compounds in a reaction material for an transesterification can be removed. A device having other removal means such as film separation, evaporation, and extraction may be provided instead of the packed device 25 and the removal may be performed by the device.

Before the removal step, fat and oil that are raw materials are subjected to a degumming process in which a gum component included in the fat and oil, such as phospholipid and protein, is removed. The degumming process is a conventional and well-known process. Specifically, the degumming process is a step of adding phosphoric acid, sulfuric acid, hydrochloric acid, boric acid or citric acid and water to fat and oil and a hydrated gum component is removed by centrifugal separation.

(Solid-Liquid Separation Step)

The following explains the solid-liquid separation step in the solid-liquid separator 29 in FIG. 2. The solid-liquid separation step is a step of removing a solid material mainly made of sterols from the reaction liquid obtained in the reaction step or from the reaction liquid which has been subjected to the alcohol stripping step and consequently has reduced unreacted alcohol. In the present specification, a sterol indicates alcohol with a steroid skeleton that is known to exist as a minor constituent in animal/plant oil etc., and an ester compounds thereof. Further, here, removal of a solid material indicates not only complete removal of the solid material in the reaction liquid, but also removal of at least part of the solid material.

The solid-liquid separation step is carried out in such a manner that the reaction liquid obtained in the reaction step or the reaction liquid which has been subjected to the alcohol stripping step and consequently has reduced unreacted alcohol is caused to pass through a solid-liquid separator. The solid-liquid separator 29 is not particularly limited as long as it can remove sterols deposited in the reaction liquid. For example, a filter, a centrifugal separator, a sedimentation tank etc. may be used. Among them, a filter is preferable in terms of energy efficiency and the scale of a device. Examples of the filtration type include: a media filtration such as a screen filtration (e.g. membrane filtration and microstrainer), a deep bed filtration (e.g. particle bed filtration and fiber bed filtration); a cake filtration such as vacuum filtration, a pressure filtration (drum type, disc type, horizontal type, leaf type, candle type etc.), a filter press, a roll (belt) press, and a screw press. Among them, the media filtration is preferable in terms of concentration of a solid material in the reaction liquid, particle size, device costs and running costs. Filtration rating of the filter is not particularly limited as long as it can remove solid materials to such an extend that the effect of the solid-liquid separation step is yielded. In terms of particle size of the solid materials, the filtration rating is preferably not more than 100 µm, more preferably not more than 50 µm, and still more preferably not more than 10 µm, and most preferably not more than 5 µm. Further, in order to assure a sufficient flow of a liquid, the lower limit of the filtration rating is preferably not less than 0.1 µm, and more preferably not less than 1 µm. In the present specification, "filtration rating" indicates an ability of a filter that can collect not less than 99.9% of a solid material with a minor axis equal to or larger than the value of the filtration rating. That is, a filter whose filtration rating is 5 µm can remove not less than 99.9% of a solid material with a minor axis equal to or larger than 5 µm that is included in a reaction liquid supplied to the solid-liquid separation step.

It is preferable that the solid-liquid separation step is carried out after the separation step. In the separation step, along with separation of the unreacted alcohol from the reaction liquid, solubility of sterols in the reaction liquid drops, making solid sterols more likely to deposit. For that reason, when the solid-liquid separation step is carried out after the separation step, it is possible to satisfactorily remove solid sterols. Further, solubility of sterols depends on a temperature. In order to remove sterols more effectively, the solid-liquid separation step is carried out preferably at 100° C. or less, more preferably at 80° C. or less, and still more preferably at 60° C. or less. The lower limit of the temperature is preferably 30° C. or more, and more preferably 40° C. or more, in order to carry out the solid-liquid separation step at a temperature where intermediate glycerides in the reaction liquid do not deposit.

In the present embodiment, an explanation was made as to a case where one solid-liquid separator 29 is provided between the reactor 26 and the phase separator 32. However, the present invention is not limited to this case. For example, a plurality of solid-liquid separators 29 may be provided. The plurality of solid-liquid separators 29 may be provided at the same position on a flow path of the reaction liquid, or may be provided at different positions, respectively. Further, when a plurality of filters are provided at the same position, it is preferable that the filters are positioned in parallel with respect to a flow of the reaction liquid. This positioning is advantageous in that when one of the filters drops its filtering ability, by controlling the flow of the reaction liquid so that the reaction liquid flows to the other filter, it is possible to avoid complete stopping of the operation of the production device. Therefore, the present embodiment can provide a production device with higher operation efficiency.

(Solid Catalyst, Alcohol, and Fat and Oil)

An explanation is made as to a solid catalyst, alcohol, and fat and oil that can be preferably employed in the present invention.

(Solid Catalyst)

It is preferable that a solid catalyst preferably used in the present invention is a catalytic compound that hardly dissolves in a reaction liquid containing raw materials and products in a transesterification, and is a solid catalyst having insolubility with respect to a reaction liquid containing fat and oil and alcohol as raw materials and fatty acid alkyl ester and glycerin as products. "Insolubility" of the solid catalyst of the present specification etc. indicates that an active ingredient (e.g., active metal ingredient) is 1000 ppm or less, preferably 800 ppm or less, more preferably 600 ppm or less, still more preferably 300 ppm or less, and most preferably not detected by an analyzer. Concentration (elution amount) of the active ingredient of the insoluble solid catalyst in the reaction liquid can be measured through X-ray Fluorescence Analysis (XRF). In the X-ray Fluorescence Analysis, it is possible to use a reaction liquid after reaction without changing a liquid state thereof. In a case of measuring a minuter elution amount, the measurement may be performed through Inductively Coupled Plasma Optical Emission Spectrometry (ICP-OES).

It is preferable that the solid catalyst preferably used in the present invention can be easily removed from the reaction system after the transesterification between the fat and oil and the alcohol. Further, it is preferable that the solid catalyst is a catalyst having activity with respect to an esterification reaction of free fatty acid contained in the fat and oil, i.e., a catalyst having activity with respect to both of a transesterification of glyceride contained in the fat and oil and an esterification reaction of free fatty acid contained in the fat and oil. This allows simultaneously performing the transesterification and the esterification reaction even when the fat and oil that are raw materials contain free fatty acid. This allows increasing the yield of fatty acid alkyl ester without separately performing esterification reaction and the transesterification.

Specific examples of the solid catalyst preferably used in the present invention include alkali metal compound, alkali earth metal compound, aluminum-containing compound, silicon-containing compound, titanium-containing compound, vanadium-containing compound, chrome-containing compound, manganese-containing compound, iron-containing compound, cobalt-containing compound, nickel-containing compound, copper-containing compound, zinc-containing compound, zirconium-containing compound, niobium-containing compound, molybdenum-containing compound, tin-containing compound, rare earth-containing compound, tungsten-containing compound, lead-containing compound, bismuth-containing compound, and ion exchange resin.

The above compound is not particularly limited as long as it contains the above essential component. Preferable examples of the form of the compound include single oxide, mixed oxide, complex oxide, hydrosulfate, phosphate, cyanide, halide, and complex. Among them, single oxide, mixed oxide, complex oxide, and cyanide are more preferable. Specific examples include aluminum oxide, titanium oxide, manganese oxide, zinc oxide, zirconium oxide, mixed and/or complex oxide among these oxides or between these oxides and other metals, zinc cyanide, iron cyanide, cobalt cyanide, mixed and/or complex cyanide among these cyanides or between these cyanides and other metals. These may be supported by a supporter or be fixed on the supporter. Examples of the supporter include silica, alumina, silica-alumina, zeolite, activated carbon, diatomite, zirconium oxide, titanium oxide, tin oxide, and lead oxide.

An example of the ion exchange resin is anion exchange resin etc. Specific examples of the anion exchange resin include strong base anion resin and weak base anion resin. When anion exchange resin is classified in terms of the degree of crosslinking or porosity, the anion exchange resin may be of gel type, porous type, high-porous type etc.

(Fat and Oil)

Fat and oil preferably used in the present invention are not particularly limited as long as they contain an ester between fatty acid and glycerin, serve as raw materials for fatty acid alkyl ester and/or glycerin in combination with alcohol, and contain an ester between fatty acid and glycerin that is so-called "fat and oil." Normally, it is preferable to use fat and oil that contain triglyceride (triester of glycerin and higher fatty acid) as a main component and contains small amounts of sub components such as diglyceride, monoglyceride, free fatty acid etc. Alternatively, fat and oil such as triolein and tripalmitin may be used.

Specific examples of such fat and oil include: plant fats and oils such as coconut oil, coleseed oil, sesame oil, soy bean oil, corn oil, sunflower oil, palm oil, palm kernel oil, safflower oil, linseed oil, cotton seed oil, tung oil, and castor oil; animal fats and oils such as beef tallow, lard, fish oil, and whale oil; and used edible oils (wasted edible oils). These fats and oils may be used singularly or two or more of them may be used in combination.

In a case where the fats and oils contain impurities such as phospholipid and protein, it is preferable to add mineral acid such as sulfuric acid, nitric acid, phosphoric acid, and boric acid in order to remove the impurities. In the method of the present invention for producing fatty acid alkyl ester and/or glycerin, it is more preferable to use a catalyst whose catalysis is less likely to be prevented by mineral acid since the catalyst allows effectively producing fatty acid alkyl ester and/or glycerin even when fat and oil contain mineral acid.

(Alcohol)

In a case of targeting the production of biodiesel, alcohol preferably used in the present invention is preferably alcohol having 1-6 carbon atoms, and more preferably alcohol having 1-3 carbon atoms. Examples of the alcohol having 1-6 carbon atoms include methanol, ethanol, propanol, isopropyl alcohol, 1-butanol, 2-butanol, t-butyl alcohol, 1-pentanol, 3-pentanol, 1-hexanol, and 2-hexanol. Among them, methanol or ethanol is preferable. These alcohols may be used singularly or two or more of them may be used in combination.

In the method of the present invention for producing fatty acid alkyl ester and/or glycerin, a minor constituent other than the fat and oil, the alcohol, and the solid catalyst may exist.

"Alcohol" in the present specification etc. is a general term indicative of a component in which hydrogen atoms of carbon hydrogen are replaced with hydroxyl groups.

The present invention is not limited to the description of the embodiments above, but may be altered by a skilled person within the scope of the claims. An embodiment based on a proper combination of technical means disclosed in different embodiments is encompassed in the technical scope of the present invention.

The following further details the present invention with reference to Examples. The present invention is not limited to these Examples and may be altered in minor parts.

EXAMPLES

Example 1

In the present Example, palm oil (fat and oil) and methanol (alcohol) were used as reaction materials. The palm oil used here was degummed palm oil obtained by adding phosphoric acid and thus precipitating and removing protein and phospholipid included in the palm oil beforehand. The ratio of free fatty acid contained in the used palm oil was 5.1 wt % and the moisture content was 0.06 wt %.

The yields of produced fatty acid methyl ester (fatty acid alkyl ester) and glycerin were calculated as follows.

> Yield of fatty acid methyl ester=(mol number of fatty acid alkyl ester in upper phase (ester phase) extracted from the second phase separator 24)/(mol number of triglyceride×3+mol number of diglyceride×2+mol number of monoglyceride each at entrance of the first reactor 10).
>
> Yield of glycerin=(mol number of glycerin in lower phase (glycerin phase) extracted from the second phase separator 24)/(sum of mol numbers of glycerides at entrance of the first reactor 10)

(Preparation of Catalyst)

The following explains the catalyst used in the present Example. Manganese carbonate (30 parts), anatase titanium oxide (19 parts), and alkyl cellulose (1 part; metolose 90SH-15000 manufactured by Shin-Etsu Chemical Co., Ltd.) were mixed sufficiently. 19 parts of water was added evenly to the mixed powders in several numbers and the mixture was further mixed and then extruded out of a hole of 0.4 mm in diameter by a wet-type extrusion granulator (Dome Gran DG-L1 manufactured by Fuji Paudal co., ltd). The extruded mixture was dried at 120° C. for one day and one night, sheared by a fine pulverizer (sample mill manufactured by Fuji Paudal co., ltd) to have a length of approximately 5 mm, and baked at 1000° C. for 5 hours in the air atmosphere. Thus, catalyst $MnTiO_3$ was obtained.

(Production of Fatty Acid Alkyl Ester and Glycerin)

Fatty acid alkyl ester and glycerin were produced with use of the production device illustrated in FIG. 1. The method for the production is specifically explained below. Palm oil (2.5 kg/h) and methanol (2.5 kg/h) were continuously flowed with use of a constant flow pump and their temperatures and their pressures were increased up to 200° C. and 5 MPa, respectively, by a heat exchanger. These liquids were mixed with each other by a mixer and the mixture was continuously flowed downward from the upper part of the first reactor 10. The material balance before and after the reaction was shown in Table 1. The reaction liquid obtained in the first reactor 10 was supplied to the first high pressure flash tower 11. The pressure of the first high pressure flash tower 11 was 0.35 MPa. Then, a heavy liquid continuously extracted from the bottom of the first high pressure flash tower 11 was supplied to the first low pressure flash tower 12.

Unreacted methanol (1.72 kg/h) continuously extracted from the top of the first high pressure flash tower 11 was supplied to the heat exchanger 30 and heat of the unreacted methanol was recovered with the heat exchanger 30 and then the unreacted alcohol was supplied to the alcohol refining tower 13.

Unreacted methanol (0.25 kg/h) continuously extracted from the top of the first low pressure flash tower 12 was supplied to the heat exchanger for increasing the temperature of methanol used in the first reaction step and heat of the unreacted methanol was recovered in the heat exchanger and then the unreacted methanol was supplied to the alcohol refining tower 13.

The heavy liquid extracted from the bottom of the first low pressure flash tower 12 was supplied to the heat exchanger for increasing the temperature of palm oil used in the first reaction step and heat of the heavy liquid was recovered in the heat exchanger and then the heavy liquid was supplied to the first phase separator 14 and subjected to phase-separation. The upper phase (fatty acid alkyl ester phase) extracted from the first phase separator 14 included 87.1% of fatty acid methyl ester, 2.4% of triglyceride, 1.1% of diglyceride, 3.5% of monoglyceride, and 5.4% of methanol. The lower phase (glycerin phase) included 58.2% of glycerin, 0.3% of fatty acid methyl ester, 0.4% of monoglyceride, and 41.1% of methanol.

Subsequently, the upper phase (fatty acid alkyl ester phase) (2.67 kg/h) extracted from the first phase separator 14 and methanol (2.36 kg/h) were heated up to 200° C. and pressured to 5 MPa by a heat exchanger. These liquids were mixed with each other by a mixer, and continuously flowed downward from the upper part of the second reactor 20. Table 1 shows the material balance before and after the reaction.

The reaction liquid obtained in the second reactor 20 was supplied to the second high pressure flash tower 21. The pressure of the second high pressure flash tower 21 was 0.35 MPa. Then, the heavy liquid continuously extracted from the bottom of the second high pressure flash tower 21 was supplied to the second low pressure flash tower 22.

Unreacted methanol (1.85 kg/h) continuously extracted from the top of the second high pressure flash tower 21 was supplied to the heat exchanger 31 and heat of the unreacted methanol was recovered in the heat exchanger 31. Further, the unreacted methanol was supplied to the heat exchanger for increasing the temperature of methanol used in the second reaction step and heat of the unreacted methanol was recovered in the heat exchanger and then supplied to the alcohol storage tank 3.

Next, the heavy liquid extracted from the bottom of the second low pressure flash tower 22 and the lower phase (glycerin phase) extracted from the first phase separator 14 were mixed with each other and the mixture was supplied to the alcohol evaporator 23. The alcohol evaporator 23 was a thin film evaporator. The pressure here was 0.034 MPa and the temperature of a heater was 175° C. The unreacted methanol extracted from the top of the alcohol evaporator 23 was supplied to the alcohol refining tower 13.

The heavy liquid extracted from the bottom of the alcohol evaporator 23 was supplied to the heat exchanger for increasing the temperature of the reaction liquid used in the second reaction step (i.e., the upper phase extracted from the first phase separator 14) and heat of the heavy liquid was recovered in the heat exchanger and then the heavy liquid was supplied to the second phase separator 24 and subjected to phase-separation. The upper phase (fatty acid alkyl ester phase) extracted from the second phase separator 24 included 99.4% of fatty acid alkyl ester, 0.10% of triglyceride, 0.06% of diglyceride, 0.41% of monoglyceride, and 0.05% of methanol. The lower phase (glycerin phase) included 99.7% of glycerin and 0.3% of methanol.

In Example 1, the yield of fatty acid alkyl ester was 99.5% and the yield of glycerin was 98.9%.

Subsequently, in the alcohol refining tower 13, methanol was refined from unreacted methanol extracted from the tops of the first pressure flash tower 11, the first low pressure flash tower 12, and the alcohol evaporator 23. In the present Example, the alcohol refining tower 13 was a distillation column whose number of plates was 15, the reflux ratio thereof was 0.25, the bottom operation temperature was 74° C., and the operation pressure was a normal pressure. All the amount of heat required in the alcohol refining tower 13 was compensated by the quantity of heat of the unreacted methanol extracted from the tops of the first high pressure flash tower 11 and the second high pressure flash tower 21. Methanol whose water content was 200 ppm was obtained from the top of the alcohol refining tower 13 and was reused as a reaction material. Table 2 shows the amount of heat required in each step.

TABLE 1

| Flow amount (kg/hr) | First reactor entrance | First reactor exit | Second reactor entrance | Second reactor exit |
|---|---|---|---|---|
| Triglyceride | 2.420 | 0.064 | 0.064 | 0.002 |
| Diglyceride | 0.077 | 0.031 | 0.031 | 0.001 |
| Monoglyceride | 0.003 | 0.106 | 0.106 | 0.010 |
| Fatty acid Ester | 0.000 | 2.325 | 2.325 | 2.494 |
| Glycerin | 0.000 | 0.226 | 0.013 | 0.048 |
| Methanol | 2.500 | 2.249 | 2.500 | 2.482 |
| Sum | 5.000 | 5.000 | 5.039 | 5.039 |

TABLE 2

| Quantity of heat (kJ) | Ex 1 and 2 | Com Ex 1 | Ex 3 |
|---|---|---|---|
| Increase in temperature and pressure in first reaction step | 2400 | 2900 | 2700 |
| Increase in temperature and pressure in second reaction step | 1700 | 2800 | 1900 |
| Alcohol evaporation step (Alcohol evaporator 23) | 1000 | 1000 | 1200 |
| Alcohol refining step (Alcohol refining tower 13) | 0 | 2700 | 0 |
| Sum | 5100 | 10400 | 5800 |

Comparative Example 1

There was performed the same operation as Example 1 except that the heat was not recovered in Comparative Example 1. The amount of heat required in each step is shown in Table 2.

Example 2

Heat of unreacted methanol continuously extracted from the tops of the first high pressure flash tower 11 and the first low pressure flash tower 12 was recovered in the same operation as Example 1 and then the unreacted methanol was supplied to the alcohol storage tank 3.

Further, Heat of unreacted methanol continuously extracted from the tops of the second high pressure flash tower 21 and the second low pressure flash tower 22 was recovered in the same operation as Example 1 and then the unreacted methanol was supplied to the alcohol refining tower 13.

Fatty acid methyl ester and glycerin were produced in the same manner as Example 1 except for the above operations. In Example 2, the reflux ratio of the alcohol refining tower 13 was 0.16, the bottom operation temperature was 80° C., and the operation pressure was a normal pressure.

In Example 2, all the amount of heat required in the alcohol refining tower 13 could be compensated by the amount of heat of unreacted methanol extracted from the tops of the first high pressure flash tower 11 and the second high pressure flash tower 21. Further, methanol whose water content was 470 ppm was obtained from the top of the alcohol refining tower 13, and the methanol could be reused as a reaction material.

Example 3

Without using the first high pressure flash tower 11, the heavy liquid extracted from the bottom of the first low pressure flash tower 12 was supplied to the first phase separator 14. The pressure here was 0.25 MPa.

Further, without using the second low pressure flash tower 22, the heavy liquid extracted from the bottom of the second high pressure flash tower 21 was supplied to the alcohol evaporator 23. The pressure here was 0.25 MPa.

Further, unreacted methanol extracted from the tops of the first pressure flash tower 11 and the alcohol evaporator 23 was supplied to the alcohol refining tower 13.

Fatty acid methyl ester and glycerin were produced in the same manner as Example 1 except for the above operations. In Example 3, the reflux ratio of the alcohol refining tower 13 was 0.29, the bottom operation temperature was 83° C., and the operation pressure was a normal pressure.

In Example 3, the purity of fatty acid methyl ester was 99.3%. In addition, 0.90% of triglyceride, 0.06% of diglyceride, 0.50% of monoglyceride, and 0.05% of methanol were contained.

In Example 3, all the amount of heat required in the alcohol refining tower 13 could be compensated by the amount of heat of the unreacted methanol extracted from the tops of the first high pressure flash tower 11 and the second high pressure flash tower 21. Further, methanol whose water content was 370 ppm was obtained from the top of the alcohol refining tower 13, and the methanol could be reused as a reaction material. The amount of heat required in each step is shown in Table 2.

Comparative Example 2

Without using the first high pressure flash tower 11, the heavy liquid extracted from the bottom of the first low pressure flash tower 12 was supplied to the first phase separator 14.

Further, without using the second high pressure flash tower 21, the reaction liquid obtained in the second reactor 20 was supplied to the second low pressure flash tower 22. Unreacted methanols continuously extracted from the tops of the first low pressure flash tower 12 and the second low pressure flash tower 22 were supplied to the heat exchangers 30 and 31, respectively, and the heat of the unreacted methanols was recovered.

Further, unreacted methanols extracted from the tops of the first normal pressure flash tower 12 and the alcohol evaporator 23 were supplied to the alcohol refining tower 13.

Fatty acid methyl ester and glycerin were produced in the same manner as Example 1 except for the above operations.

The condensation temperature of unreacted methanols continuously extracted from the tops of the first low pressure flash tower 12 and the second low pressure flash tower 22 was 64° C., and the bottom temperature of the alcohol refining tower 13 increased only up to 54° C. That is, it was impossible to refine alcohol in the alcohol refining tower 13.

Example 4

In the present example, palm oil and methanol were used as reaction materials. The palm oil was degummed palm oil obtained by adding phosphoric acid and thus precipitating and removing protein and phospholipid. The percentage of free fatty acid contained in the palm oil was 5.1 wt % and the percentage of moisture content contained in the palm oil was 0.06 wt %.

The yields of fatty acid alkyl ester and glycerin were calculated with use of equations that are the same as those in Example 1. The solid catalyst used here was MnTiO3 catalyst.

Fatty acid alkyl ester and glycerin were produced with use of the production device 1 as illustrated in FIG. 1. Palm oil (2.5 kg/h) and methanol (2.5 kg/h) were mixed with each other by a constant flow pump and was continuously flowed downward from the upper part of the first reactor 10. The pressure in the reactor was 5 MPa and the temperature in the reactor was 200° C. The material balance before and after the reaction is shown in Table 3.

TABLE 3

| Flow amount (kg/hr) | First reactor entrance | First reactor exit | Second reactor entrance | Second reactor exit |
|---|---|---|---|---|
| Triglyceride | 2.420 | 0.064 | 0.064 | 0.002 |
| Diglyceride | 0.077 | 0.031 | 0.031 | 0.001 |
| Monoglyceride | 0.003 | 0.106 | 0.106 | 0.010 |
| Fatty acid ester | 0.000 | 2.325 | 2.325 | 2.494 |
| Glycerin | 0.000 | 0.226 | 0.013 | 0.048 |
| MeOH | 2.500 | 2.249 | 2.500 | 2.482 |
| Sum | 5.000 | 5.000 | 5.039 | 5.039 |

The reaction liquid obtained in the first reactor 10 was supplied to the first high pressure flash tower 11. The pressure of the first high pressure flash tower 11 was 0.35 MPa. The heavy liquid continuously extracted from the bottom of the first high pressure flash tower included 16.6% of methanol. The heavy liquid was supplied to the first low pressure flash tower 12. The heavy liquid extracted from the bottom of the first low pressure flash tower 12 included 9.7% of methanol.

The heavy liquid extracted from the bottom of the first low pressure flash tower 12 was supplied to the separator 14 and was subjected to phase-separation. The upper phase (fatty acid alkyl ester phase) extracted from the separator 14 contained 87.1% of fatty acid methyl ester, 2.4% of triglyceride, 1.1% of diglyceride, and 3.5% of monoglyceride, and 5.4% of methanol. The lower phase (glycerin phase) contained 58.2% of glycerin, 0.3% of fatty acid methyl ester, 0.4% of monoglyceride, and 41.4% of methanol. The upper phase (fatty acid alkyl ester phase) (2.67 kg/h) extracted from the separator 14 and methanol (2.36 kg/h) were mixed with each other and the mixture was continuously flowed downward from the upper part of the second reactor 20. The pressure in the reactor was 5 MPa and the temperature in the reactor was 200° C. The material balance before and after the reaction is shown in Table 3.

The reaction liquid obtained in the second reactor 20 was supplied to the second high pressure flash tower 21. The pressure of the second high pressure flash tower 21 was 0.35 MPa. The heavy liquid continuously extracted from the bottom of the second high pressure flash tower contained 14.4% of methanol.

The heavy liquid extracted from the bottom of the second low pressure flash tower 22 and the lower phase (glycerin phase) extracted from the separator 14 were mixed with each other and the mixture was supplied to the alcohol evaporator 23. The alcohol evaporator 23 was a thin evaporator. The pressure was 0.034 MPa and the temperature of a heater was 175° C. The residence time of the liquid at that time was 2 minutes. The heavy liquid continuously extracted from the bottom of the alcohol evaporator 23 contained 0.07% of methanol.

The heavy liquid extracted from the bottom of the alcohol evaporator 23 was supplied to the separator 24 and was subjected to phase-separation. The upper phase (fatty acid alkyl ester phase) extracted from the separator 24 contained 99.4% of fatty acid methyl ester, 0.10% of triglyceride, 0.06% of diglyceride, 0.41% of monoglyceride, and 0.05% of methanol. The lower phase (glycerin phase) contained 99.7% of glycerin and 0.3% of methanol.

The yield of fatty acid alkyl ester was 99.5% and the yield of glycerin was 98.9%.

Comparative Example 3

There was performed the same operation as Example 4 except that methanol was evaporated with use of an evaporator having a compulsory circulating heat exchanger as the alcohol evaporator 23. The residence time in the alcohol refining tower 23 was 116 minutes. A reverse reaction occurred and 0.65% of fatty acid methyl ester was decomposed. The yield and the purity of fatty acid methyl ester were 98.9% and 98.6%, respectively. The fatty acid methyl ester contained 0.32% of triglyceride, 0.18% of diglyceride, 0.80% of monoglyceride, and 0.12% of methanol. The yield and the purity of glycerin were 98.1% and 99.2%, respectively.

Comparative Example 4

There was performed the same operation as Example 4 except that a liquid extracted from the bottom of the second low pressure flash tower 22 was supplied to the separator 24, the upper phase (fatty acid alkyl ester phase) obtained in the separator 24 was evaporated by the alcohol evaporator 23, and a mixture liquid of the lower phase of the separator 14 and the lower phase of the separator 24 was evaporated by a new alcohol evaporator. 0.22% of fatty acid methyl ester was distributed to the glycerin phase in the second phase separator 24. The yield and the purity of fatty acid methyl ester were 99.3% and 99.4%, respectively. The yield and the purity of glycerin were 98.9% and 97.7%, respectively. Glycerin contained 2.1% of fatty acid methyl ester.

Example 5

Method for Preparing Solid Catalyst

Manganese carbonate (239 g), anatase titanium oxide (152 g), and alkyl cellulose (metolose 90SH-15000 manufactured by Shin-Etsu Chemical Co., Ltd.) were mixed sufficiently. 150 g of water was added evenly to the mixed powders in several numbers and the mixture was further mixed and then extruded out of a hole of 0.4 mm in diameter by a wet-type extrusion granulator (Dome Gran DG-L1 manufactured by Fuji Paudal co., ltd). The extruded mixture was dried at 120° C. for one day and one night, sheared by a fine pulverizer (sample mill manufactured by Fuji Paudal co., ltd) to have a length of approximately 5 mm, and baked at 1000° C. for 5 hours in the air atmosphere. Thus, catalyst MnTiO3 was obtained.

An SUS-316 straight reaction tube of 10 mm in inner diameter and 210 mm in length was filled with 15 mL of the obtained solid catalyst. An exit of the reaction tube was provided with a filter and a back pressure regulator via an air-cooling tube so that the pressure could be controlled.

(Fat and Oil and Alcohol to be Used)

Palm oil was used as fat and oil and methanol was used as alcohol. The palm oil was refined palm oil having been degummed.

(Production Method)

Palm oil (flow amount: 6.3 g/h) and methanol (flow amount: 6.3 g/h) were drawn by a constant flow pump from a palm oil storage tank for storing palm oil and a methanol storage tank for storing methanol, respectively, and are mixed with each other. The mixed palm oil and methanol was caused to pass the SUS-316 straight-tube-packed device of 10 mm in inner diameter and 210 mm in length that is filled with an adsorber (15 mL), and then caused to continuously flow downward from the upper part of the reaction tube. In this process, the pressures in the packed device and the reaction tube were set to 5 MPa with use of the back pressure regulating valve. The amount of methanol supplied with respect to palm oil was 9 times larger than the theoretically required amount. Internal temperatures of the packed device and the reaction tube were set to 200° C. by heating from the outside.

(Adsorber)

In the present Example, the adsorber was 70-180 μm spherical silica of CARiACT Q-50 manufactured by Fuji Silysia Chemical Ltd.

(Measurement of Activity of Solid Catalyst)

Measurement of activity of MnTiO3 was performed by measuring the conversion rate of palm oil and the yield of fatty acid methyl ester when the reaction times were 210 hours, 402 hours, 642 hours, and 843 hours. In the present example, the conversion rate of palm oil and the yield of fatty acid methyl ester were calculated in accordance with the following equation.

Conversion rate of palm oil (%)=(mol number of consumed palm oil at time when reaction was finished)/(mol number of prepared palm oil)×100

Yield of fatty acid methyl ester (%)=(mol number of generated fatty acid methyl ester at time when reaction was finished)/(mol number of effective fatty acid at time it was prepared)×100

The effective fatty acid indicates triglyceride, diglyceride, monoglyceride, and free fatty acid of fatty acid contained in the palm oil. That is, the mol number of the effective fatty acid at a time it was prepared can be calculated in accordance with the following equation.

Mol number of effective fatty acid at time when it was prepared (mol)=[amount of prepared palm oil (g)×ssaponification value of palm oil (mg (KOH)/g (palm oil))/56100]

Further, the adsorber and the catalyst that have been subjected to the reaction for 1000 hours were analyzed through X-ray Fluorescence Analysis (XRF). The result of the analysis showed that the adsorber adsorbed 8 mg of phosphorous and phosphorous compounds and 5 mg of calcium and calcium compounds. On the other hand, the result of the analysis showed that the catalyst adsorbed 25 mg of phosphorous and phosphorous compounds and 2 mg of calcium and calcium compounds.

(Measurements of Phosphorous Concentration and Calcium Concentration)

The measurements of phosphorous concentration and calcium concentration were performed through Inductively Coupled Plasma Mass Spectrometer (ICP-MS). Specifically, a reaction raw material to be measured (2 g) was put in a Teflon® beaker and then subjected to thermolysis with use of sulfuric acid, nitric acid, perchloric acid, and hydrogen peroxide solution, and subjected to heat dissolution with use of diluted nitric acid so that the aqueous solution filled up the beaker. The obtained aqueous solution was measured through ICP-MS so that phosphorous concentration and calcium concentration were measured.

The result of the measurement showed that phosphorous concentration was 1.5 ppm (μg/g) and calcium concentration was 0.2 ppm (μg/g) in the reaction raw material. At that time, quantitation limits of phosphorous and calcium in consideration of the result of a blank test were 0.4 ppm and 0.06 ppm, respectively.

Comparative Example 5

Production of fatty acid methyl ester and glycerin and measurement of activity of a solid catalyst were performed with use of the same materials and through the same method as Example 5 except that the process for mixing palm oil and methanol and causing the mixture to pass the packed device was omitted in Comparative Example 5. In Comparative Example 5, measurement of activity of MnTiO3 was performed when the reaction times were 216 hours, 408 hours, 599 hours, and 840 hours.

In Comparative Example 5, phosphorous concentration and calcium concentration of the reaction raw material were 2.5 ppm (μg/g) and 1.0 ppm (μg/g), respectively.

Further, the adsorber and the catalyst that have been subjected to the reaction for 1000 hours were analyzed through X-ray Fluorescence Analysis (XRF). The result of the analysis showed that the catalyst adsorbed 35 mg of phosphorous and phosphorous compounds and 7 mg of calcium and calcium compounds.

(Result of Measuring Activity of Solid Catalyst)

Figure 3:
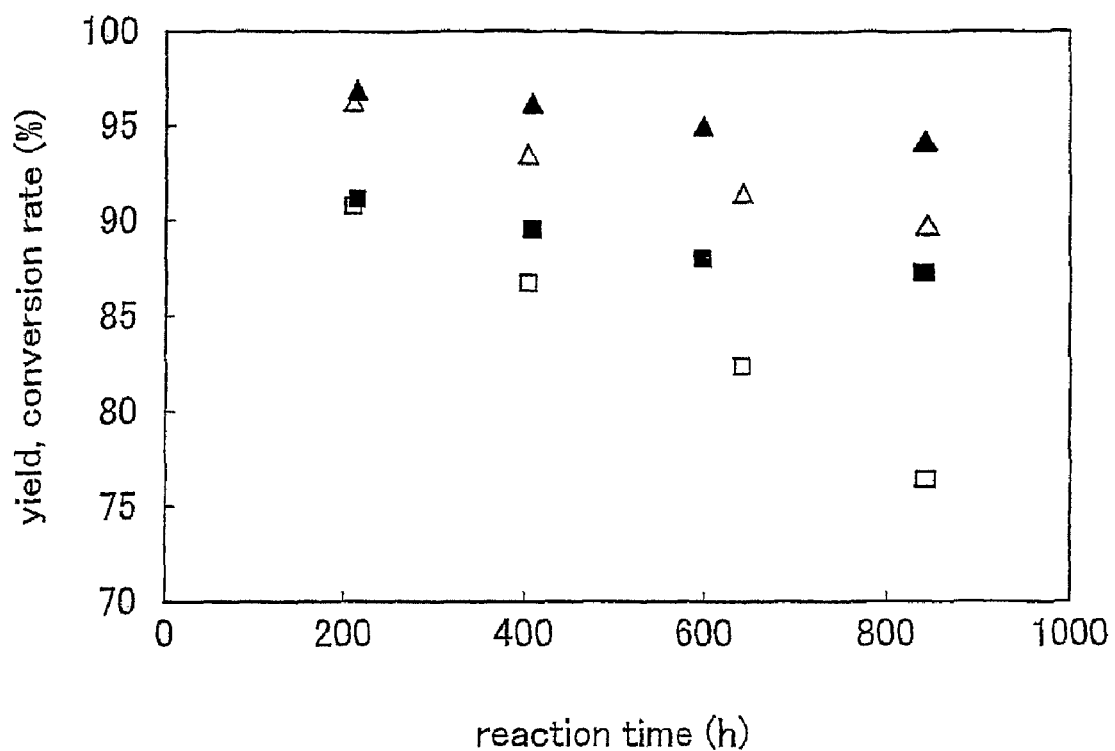
FIG. 3 is a graph showing changes of the conversion rates of palm oil and the yields of fatty acid methyl ester in Example 5 and Comparative Example 5.

FIG. 3 illustrates the result of measuring activity of the solid catalyst. FIG. 3 is a graph showing changes of conversion rates of palm oil and yields of fatty acid methyl ester at a time when reaction times change from 200 hours to 1000 hours. In FIG. 3, "black triangle" indicates the conversion rate of palm oil in Example 5, "white triangle" indicates the conversion rate of palm oil in Comparative Example 5, "black square" indicates the yield of fatty acid methyl ester in Example 5, and "white square" indicates the yield of fatty acid methyl ester in Comparative Example 5.

As illustrated in FIG. 3, in Example 5 where the reaction raw material was caused to pass the packed device in order to reduce phosphorous concentration and calcium concentration of the reaction raw material, the conversion rate of palm oil and the yield of fatty acid methyl ester dropped only by approximately 3-5%, and did not change greatly.

In contrast thereto, in Comparative Example 5 where the reaction raw material was not caused to pass the packed device and phosphorous concentration and calcium concentration of the reaction raw material were not made lower than 2.5 ppm and 1 ppm, respectively, the conversion rate of palm oil and the yield of fatty acid methyl ester changed greatly as the reaction time elapsed. The conversion rate of palm oil dropped approximately two times larger than that in Example 5, and the yield of fatty acid methyl ester dropped approximately four times larger than that in Example 5.

The results illustrated in FIG. 3 show that by reducing phosphorous concentration and calcium concentration of the reaction raw material to be less than 2.5 ppm and 1 ppm, respectively, it is possible to suppress the drop of activity of MnTiO3.

Example 6

Production of Fatty Acid Alkyl Ester and Glycerin

In the present Example, palm oil and methanol were used as reaction raw materials. The palm oil was refined palm oil having been degummed. An SUS 316 reactor (first reactor 10) of 10 mm in inner diameter and 210 mm in length was filled with a solid catalyst (15 mL).

Palm oil (6.3 g/hr) and methanol (6.3 g/hr) were continuously supplied by a constant flow pump, heated at 200° C. and mixed by a line mixer, and then caused to flow downward from the upper part of the first reactor 10. The inside of the first reactor 10 was set to have a temperature of 200° C. and a pressure of 5 MPa. In the present Example, a catalyst prepared in the same manner as Example 5 was used.

The reaction liquid obtained in the first reactor 10 was supplied to the first high pressure flash tower 11. The pressure of the first high pressure flash tower 11 was set to 0.35 MPa. Then, a heavy liquid continuously extracted from the bottom of the first high pressure flash tower 11 was supplied to the first low pressure flash tower 12. The heavy liquid continuously extracted from the first high pressure flash tower 11 contained 17% of methanol.

The heavy liquid extracted from the bottom of the first low pressure flash tower 12 was separated into the upper phase and the lower phase with use of a coalescer (oil-water separation film, first phase separator 14). Each phase was obtained as an even phase. The upper phase contained 0.05% of glycerin.

Subsequently, the obtained upper phase (6.3 g/hr) was continuously supplied to the second reactor 20 and caused to react with methanol (6.3 g/hr) under the same conditions (200° C., 5 MPa) as the first reactor 10. The second reactor 20 was filled with 6 mL of the aforementioned solid catalyst.

Then, the reaction liquid obtained in the second reactor 20 was supplied to the second high pressure flash tower 21. The pressure of the second high pressure flash tower 21 was set to 0.35 MPa. Then, the heavy liquid continuously extracted from the bottom of the second high pressure flash tower 21 was supplied to the second low pressure flash tower 22. The heavy liquid continuously extracted from the second high pressure flash tower 21 contained 14% of methanol.

The heavy liquid extracted from the bottom of the second low pressure flash tower 22 and the lower phase (glycerin phase) in the first phase separator 14 were mixed with each other and supplied to a thin film evaporator (alcohol evaporator 23) in order to diffuse unreacted methanol contained in the mixture liquid. The inside of the thin film evaporator was adjusted to have a pressure of 0.03 MPa and the temperature of a heater was adjusted to be 175° C. The residence time was set to 2 minutes. The heavy liquid continuously extracted from the bottom of the tower of the thin film evaporator contained 0.07% of methanol.

Then, the obtained heavy liquid was separated by a coalescer (oil-water separation film, second phase separator 24) into the upper phase and the lower phase. The obtained upper phase contained fatty acid methyl ester (whose purity was more than 99%) and the obtained lower phase contained glycerin (whose purity was more than 99%). Here, glycerin concentration in the obtained upper phase was less than 0.05 wt % and monoglyceride concentration in the obtained upper phase was 0.25 wt %. That is, concentration of fatty acid alkyl ester contained in the obtained upper phase was 99.7 wt %.

In the method of the present invention for producing fatty acid alkyl ester and/or glycerin, at least a part of heat of unreacted alcohol evaporated from a reaction liquid obtained by reacting fat and oil and alcohol over a solid catalyst is used in reproduction of alcohol.

Consequently, at least a part of energy required in the alcohol refining step is obtained inside the reaction system, and therefore it is possible to reduce energy required to produce outside the reaction system. This yields an effect of reducing costs in producing fatty acid alkyl ester and glycerin over a solid catalyst.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

According to the method of the present invention for producing fatty acid alkyl ester and glycerin, it is possible to produce, cheaply, industrially, and environment-friendly, fatty acid alkyl ester applicable to biodiesel fuel, foods, cosmetics, medicines, fuels etc. and glycerin applicable to nitroglycerin, raw materials for alkyd resin, medicines, foods, paints, cosmetics etc.

The invention claimed is:

1. A method for producing fatty acid alkyl ester and/or glycerin, comprising:
    a first reaction step of reacting fat and oil with alcohol over a solid catalyst;
    a first alcohol stripping step of evaporating, from a first reaction liquid obtained in the first reaction step, unreacted alcohol that remains without reacting in the first reaction step; and
    an alcohol refining step of refining the alcohol from the unreacted alcohol with use of at least a part of heat of the unreacted alcohol, and
    applying at least two stages of pressures that are different from each other in the first alcohol stripping step.

2. The method as set forth in claim 1, wherein a first stage of the pressures in the first alcohol stripping step ranges from 0.15 to 1.5 MPa.

3. The method as set forth in claim 1, further comprising:
    a second reaction step of reacting fat and oil with alcohol over a solid catalyst, the fat and oil being contained in an upper phase obtained by phase-separating refined products obtained in the first alcohol stripping step; and
    a second alcohol stripping step of evaporating, from a second reaction liquid obtained in the second reaction step, unreacted alcohol that remains without reacting in the second reaction step,
    in the alcohol refining step, the alcohol being refined from the unreacted alcohol evaporated in the first and second alcohol stripping steps, with use of at least a part of heat of the unreacted alcohol.

4. The method as set forth in claim 3, wherein at least two stages of pressures that are different from each other are applied in the second alcohol stripping step.

5. The method as set forth in claim 4, wherein a first stage of the pressures in the second alcohol stripping step ranges from 0.15 to 1.5 MPa.

6. The method as set forth in claim 1, wherein a substance that is contained in the alcohol obtained in the alcohol refining step and that is other than the alcohol accounts for not more than 1000 ppm of all components contained in the alcohol obtained in the alcohol refining step.

7. The method as set forth in claim 1, further comprising:
a first phase-separation step of phase-separating the first reaction liquid obtained in the first reaction step into a first fatty acid alkyl ester phase and a first glycerin phase;
a second reaction step of reacting fat and oil contained in the first fatty acid alkyl ester phase with alcohol over a solid catalyst;
a third alcohol stripping step of evaporating, from a second reaction liquid obtained in the second reaction step, unreacted alcohol that remains without reacting in the second reaction step, with use of an evaporator including a heat exchanger selected from a thin film evaporator with an agitating rotor, a thin film evaporator with tubes arranged as a bundle, and a thin film evaporator with a centrifugal rotor; and
a second phase-separation step of phase-separating refined products obtained in the third alcohol stripping step into a second fatty acid alkyl ester phase and a second glycerin phase.

8. The method as set forth in claim 1, further comprising:
a first phase-separation step of phase-separating the first reaction liquid obtained in the first reaction step into a first fatty acid alkyl ester phase and a first glycerin phase;
a second reaction step of reacting fat and oil contained in the first fatty acid alkyl ester phase with alcohol over a solid catalyst;
a third alcohol stripping step of evaporating, from a second reaction liquid obtained in the second reaction step, unreacted alcohol that remains without reacting in the second reaction step, with use of an evaporator including a heat exchanger whose residence time is 20 minutes or less; and
a second phase-separation step of phase-separating refined products obtained in the third alcohol stripping step into a second fatty acid alkyl ester phase and a second glycerin phase.

9. The method as set forth in claim 7, wherein in the third alcohol stripping step, the unreacted alcohol that remains without reacting in the first reaction step is further evaporated from the first glycerin phase with use of the evaporator.

10. The method as set forth in claim 7, wherein in the third alcohol stripping step, the unreacted alcohol that remains without reacting in the second reaction step is evaporated from the second reacting liquid obtained in the second reaction step, and the unreacted alcohol that remains without reacting in the first reaction step is evaporated from the first glycerin phase.

11. The method as set forth in claim 7, wherein a second alcohol stripping step of evaporating unreacted alcohol from the second reaction liquid is performed before the third alcohol stripping step.

12. The method as set forth in claim 7, wherein the first alcohol stripping step is performed before the first phase-separation step.

13. The method as set forth in claim 7, wherein in the third alcohol stripping step, the unreacted alcohol is evaporated in such a manner that the unreacted alcohol accounts for not more than 0.5 wt % of the refined products obtained in the third alcohol stripping step.

14. The method as set forth in claim 1, further comprising a removal step of removing at least one selected from phosphorous, phosphorous compounds, calcium, and calcium compounds that are contained in a reaction raw material including the fat and oil and the alcohol.

15. The method as set forth in claim 14, wherein in the removal step, at least one selected from phosphorous, phosphorous compounds, calcium, and calcium compounds is adsorbed and removed by an adsorber.

16. The method as set forth in claim 14, wherein in the removal step, concentration of phosphorous atoms in phosphorous and phosphorous compounds contained in the reaction raw material is less than 2.5 ppm.

17. The method as set forth in claim 14, wherein in the removal step, concentration of calcium atoms in calcium and calcium compounds contained in the reaction raw material is less than 1 ppm.

18. The method as set forth in claim 1, further comprising:
a first phase-separation step of phase-separating a refined product into a first fatty acid alkyl ester phase and a first glycerin phase with use of a separation filter, the refined product being obtained by evaporating the unreacted alcohol from the first reaction liquid in the first alcohol stripping step;
a second reaction step of reacting fat and oil contained in the first fatty acid alkyl ester phase with alcohol over a solid catalyst; and
a second phase-separation step of phase-separating a second reaction liquid obtained in the second reaction step into a second fatty acid alkyl ester phase and a second glycerin phase with use of a separation filter.

19. A device for producing fatty acid alkyl ester and/or glycerin, comprising:
a reactor for reacting fat and oil with alcohol over a solid catalyst;
a stripper for stripping, from a reaction liquid obtained in the reactor, unreacted alcohol that remains without reacting in the reactor; and
a refiner for refining the alcohol from the unreacted alcohol stripped in the stripper, with use of at least a part of heat of the unreacted alcohol, and
wherein means for applying at least two stages of pressures that are different from each other are provided in the stripper.

20. The device as set forth in claim 19, further comprising a packed device filled with an adsorber for adsorbing at least one selected from phosphorous, phosphorous compounds, calcium, and calcium compounds that are contained in a reaction raw material including the fat and oil and the alcohol, the reactor causing the reaction raw material having passed the packed device to react over a solid catalyst.

* * * * *

UNITED STATES PATENT AND TRADEMARK OFFICE
CERTIFICATE OF CORRECTION

| | | |
|---|---|---|
| PATENT NO. | : 8,039,651 B2 | |
| APPLICATION NO. | : 12/739332 | |
| DATED | : October 18, 2011 | |
| INVENTOR(S) | : Masanori Nonoguchi et al. | |

It is certified that error appears in the above-identified patent and that said Letters Patent is hereby corrected as shown below:

Cover page, item (22), PCT filing date should read "October 29, 2008" instead of "October 31, 2007".

Signed and Sealed this
Sixth Day of March, 2012

David J. Kappos
*Director of the United States Patent and Trademark Office*